United States Patent
Steines et al.

(10) Patent No.: US 9,737,367 B2
(45) Date of Patent: Aug. 22, 2017

(54) HISTORICAL PATIENT-SPECIFIC INFORMATION FOR ARTICULAR REPAIR SYSTEMS

(71) Applicant: ConforMIS, Inc., Bedford, MA (US)

(72) Inventors: Daniel Steines, Lexington, MA (US); John Slamin, Wrentham, MA (US)

(73) Assignee: ConforMIS, Inc., Billerica, MA (US)

( * ) Notice: Subject to any disclaimer, the term of this patent is extended or adjusted under 35 U.S.C. 154(b) by 0 days.

(21) Appl. No.: 14/774,970

(22) PCT Filed: Mar. 11, 2014

(86) PCT No.: PCT/US2014/023235
§ 371 (c)(1),
(2) Date: Sep. 11, 2015

(87) PCT Pub. No.: WO2014/150428
PCT Pub. Date: Sep. 25, 2014

(65) Prior Publication Data
US 2016/0015465 A1    Jan. 21, 2016

Related U.S. Application Data

(60) Provisional application No. 61/786,708, filed on Mar. 15, 2013.

(51) Int. Cl.
*A61F 2/30* (2006.01)
*A61B 17/17* (2006.01)
(Continued)

(52) U.S. Cl.
CPC .............. *A61B 19/50* (2013.01); *A61B 17/17* (2013.01); *A61B 34/10* (2016.02);
(Continued)

(58) Field of Classification Search
CPC ...... A61F 2/38; A61F 2/28; A61F 2002/2835; A61F 2/3804; A61F 2/30942; A61F 2/30
See application file for complete search history.

(56) References Cited

U.S. PATENT DOCUMENTS 9,402,726 B2 * 8/2016 Linderman ......... A61F 2/30756
2009/0270868 A1 10/2009 Park et al. ...................... 606/87
(Continued)

FOREIGN PATENT DOCUMENTS

| WO | WO 2012/112694 A2 | 8/2012 | ............... A61B 6/00 |
| WO | WO 2013/025814 A1 | 2/2013 | ............... A61F 2/38 |
| WO | WO 2014/150428 A2 | 9/2014 | ............. G06F 19/00 |

OTHER PUBLICATIONS

International Searching Authority, International Search Report—International Application No. PCT/US2014/023235 dated Sep. 24, 2014, together with the Written Opinion of the International Searching Authority, 15 pages.
(Continued)

*Primary Examiner* — Jason-Dennis Stewart
(74) *Attorney, Agent, or Firm* — Sunstein Kann Murphy & Timbers LLP

(57) ABSTRACT

Methods and systems for retention and use of historical patient-specific information in selecting and/or designing patient-adapted articular repair systems are disclosed herein. Various embodiments include articular repair system components that are selected and/or designed based, at least in part, on both current patient-specific information and historical patient-specific information. According to certain embodiments, a method of making an implant component for intended treatment of a diseased or damaged joint of a patient is disclosed.

20 Claims, 8 Drawing Sheets

(51) Int. Cl.
 *A61B 19/00* (2006.01)
 *A61B 34/10* (2016.01)
(52) U.S. Cl.
 CPC .... *A61F 2/30942* (2013.01); *A61B 2034/108* (2016.02); *A61F 2002/3069* (2013.01); *A61F 2002/3096* (2013.01); *A61F 2002/30948* (2013.01)

(56) References Cited

U.S. PATENT DOCUMENTS

| | | | |
|---|---|---|---|
| 2010/0292963 A1 | 11/2010 | Schroeder | 703/1 |
| 2011/0093108 A1 | 4/2011 | Ashby et al. | 700/103 |
| 2013/0012553 A1 | 1/2013 | MacDonald et al. | 514/365 |
| 2014/0208578 A1* | 7/2014 | Linderman | A61B 17/155 29/592 |

OTHER PUBLICATIONS

European Patent Office, Extended European Search Report—Application No. 14769907.8, dated Nov. 3, 2016, 6 pages.

* cited by examiner

US 9,737,367 B2

HISTORICAL PATIENT-SPECIFIC INFORMATION FOR ARTICULAR REPAIR SYSTEMS

RELATED APPLICATIONS

This application claims the benefit of U.S. Provisional Application No. 61/786,708, entitled "Retention and Use of Historical Patient-Specific Information for Articular Repair Systems" and filed Mar. 15, 2013, the disclosure of which is incorporated herein by reference in its entirety.

TECHNICAL FIELD

The present disclosure relates to retention and/or use of historical patient-specific information. In particular, various embodiments relate to use of historical patient-specific information for selecting and/or designing articular repair systems (e.g., resection cut strategy, guide tools, and implant components), as described in, for example, U.S. patent application Ser. No. 13/397,457, entitled "Patient-Adapted and Improved Orthopedic Implants, Designs And Related Tools," filed Feb. 15, 2012, and published as U.S. Patent Publication No. 2012-0209394, which is incorporated herein by reference in its entirety. Various embodiments also relate to use of historical patient-specific information for selecting and/or designing revisionary articular repair systems, as described in, for example, International Application Number PCT/US/12/50964, entitled "Revision Systems, Tools and Methods for Revising Joint Arthroplasty Implants," filed Aug. 15, 2012, and published as International Publication No. WO 2013/025814, which is also incorporated herein by reference in its entirety.

SUMMARY

According to certain embodiments, a method of making an implant component for intended treatment of a diseased or damaged joint of a patient is disclosed. The method includes receiving current patient-specific information associated with the joint and receiving historical patient-specific information associated with the joint. The current patient-specific information and the historical patient-specific information are used, at least in part, for selecting and/or designing the implant component.

According to certain embodiments, an implant component for treating a patient's joint is disclosed. The implant component includes a joint-facing surface having a patient-adapted dimension based, at least in part, on historical patient-specific information associated with the joint. The implant component also includes a bone-facing surface having a patient-adapted dimension based, at least in part, on current patient-specific information associated with the joint.

According to certain embodiments, a system for treating a patient's joint is disclosed. The system includes a cutting guide with a patient-adapted surface configured to engage at least a portion of a surface of the joint. The patient-adapted surface includes a shape based, at least in part, on current patient-specific information associated with the joint. The system also includes an implant component for treating a patient's joint. The implant component includes a joint-facing surface having a patient-adapted dimension based, at least in part, on historical patient-specific information associated with the joint. The implant component also includes a bone-facing surface having a patient-adapted dimension based, at least in part, on current patient-specific information associated with the joint.

According to certain embodiments, a method of providing historical patient-specific information for selecting and/or designing a treatment for a diseased or damaged joint of a patient is disclosed. The method includes receiving a first set of patient-specific information associated with a first state of at least a portion of the patient's anatomy. This first set of patient-specific information is information obtained from the patient prior to the diseased or damaged state of the joint. The first set of patient-specific information is stored in a library of historical patient-specific information. At least a portion of the historical patient-specific information is then provided for selecting and/or designing a treatment for the joint.

DETAILED DESCRIPTION

Patient-Adapted Features

Figure 1:
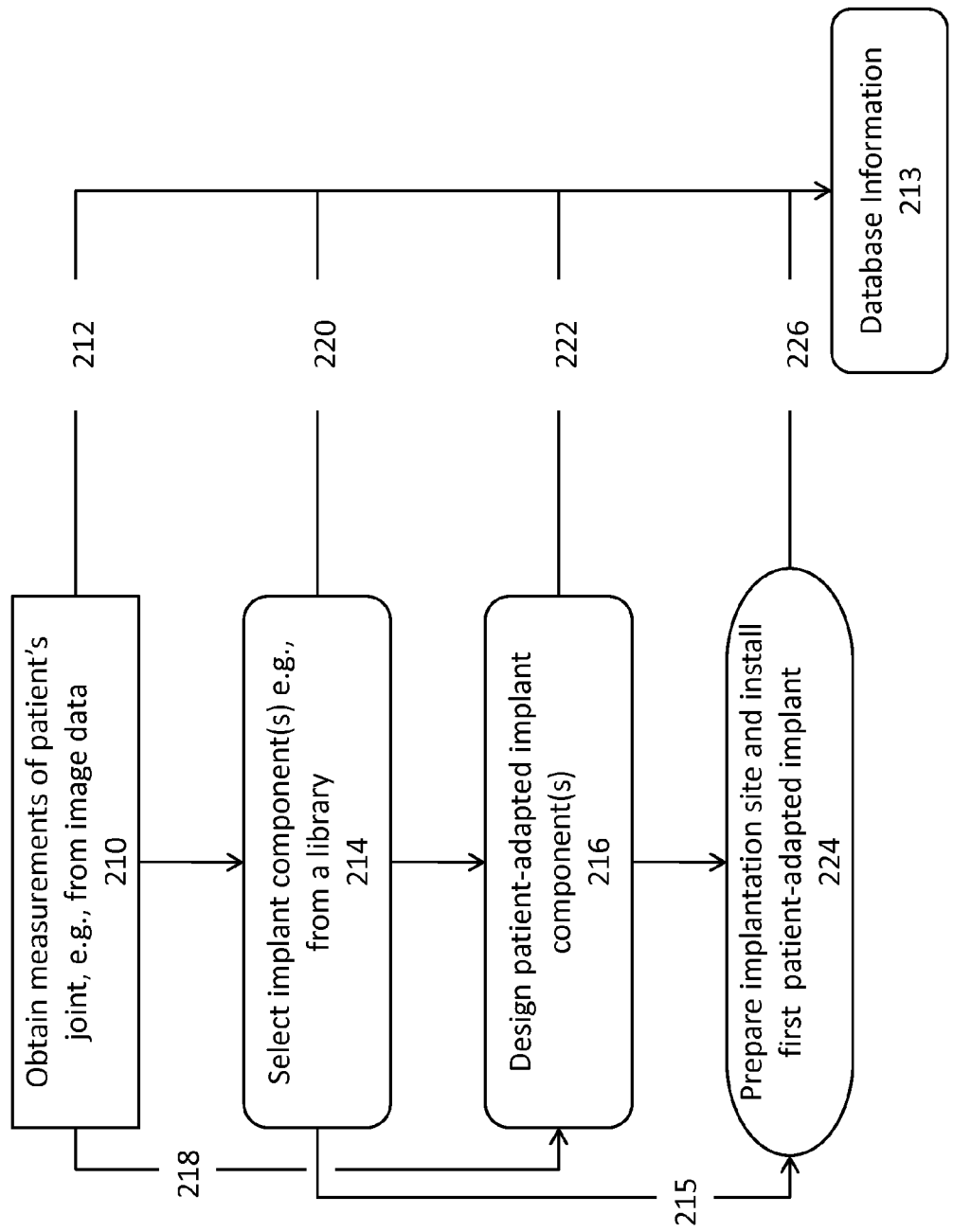
FIG. 1 is a flow chart illustrating a process that includes selecting and/or designing an initial patient-adapted implant.

Certain embodiments described herein relate to selecting and/or designing patient-adapted implants, guide tools, and related methods. Patient-adapted features of an implant component, guide tool or related implantation method can be achieved by analyzing patient-specific information (e.g., imaging test data) and selecting and/or designing (e.g., preoperatively selecting from a library and/or preoperatively designing) an implant component, a guide tool, and/or a procedure having a feature that is matched and/or optimized for the particular patient's anatomy and/or biology. Accordingly, the patient-adapted implant components, guide tools, and/or methods include one or more patient-adapted features. Patient-adapted features can include patient-specific features and/or patient-engineered features.

Certain embodiments relate to patient-specific implants, guide tools, and related methods. For example, some embodiments relate to articular implant components having one or more patient-specific features adapted to match one or more of the patient's biological features, such as one or more of biological/anatomical structures, alignments, kinematics, and/or soft tissue impingements. Accordingly, the one or more patient-specific features of an implant component can include, but are not limited to, one or more implant component surfaces, such as surface contours or angles, and one or more implant component dimensions such as thickness, width, depth, or length. The patient-specific feature(s) of an implant component can be designed based on patient-specific data to substantially match one or more of the patient's biological features (e.g., anatomical and/or biological features). In various embodiments described herein, the act of designing an implant component can include manufacturing the implant component having the related design features. For example, designing an implant component can include preoperatively establishing a design of one or more features of an implant component, for example, using a CAD computer program on a computer system specialized operated for such use and having one or more user interfaces, and instructing the transfer of that design data, for example, from a CAD computer program or computer system to a CAM (computer-aided manufacturing) computer program or computer system. Optionally, in certain embodiments, designing the implant can further include instructing the initiation of manufacturing the physical implant and/or manufacturing the implant.

Additionally or alternatively, patient-specific feature(s) of an implant component or guide tool can be achieved by analyzing imaging test data and selecting (e.g., preoperatively selecting from a library of implant components) the implant component that best fits one or more pre-determined patient-specific parameters that are derived from the imaging test.

Moreover, an implant component or guide tool can include a patient-specific feature that is both selected and designed. For example, an implant component initially can be selected (e.g., preoperatively selected from a library of implants) to have a feature with a standard or blank dimension, or with a larger or smaller dimension than the predetermined patient-specific dimension. Then, the implant component can be machined (if selected from an actual library of implant components) or manufactured (if selected from a virtual library of implant components) so that the standard dimension or blank dimension or larger-dimensioned or smaller-dimensioned implant feature is altered to have the patient-specific dimension.

In addition or alternatively, certain embodiments can include patient-engineered implants, guide tools, and related methods. Some embodiments can include articular implant components having one or more patient-engineered features optimized from patient-specific data to meet one or more parameters to enhance one or more of the patient's biological features, such as one or more biological/anatomical structures, alignments, kinematics, and/or soft tissue impingements. Accordingly, the one or more patient-engineered features of an implant component can include, but are not limited to, one or more implant component surfaces, such as surface contours, angles or bone cuts, and dimensions such as thickness, width, depth, or length of one or more aspects of the implant component. The patient-engineered feature(s) of an implant component can be designed and/or manufactured (e.g., preoperatively designed and manufactured) based on patient-specific data to substantially enhance or improve one or more of the patient's anatomical and/or biological features. Methods for preparing certain patient-engineered features are described, for example, in U.S. Ser. No. 12/712,072, entitled "Automated Systems For Manufacturing Patient-Specific Orthopedic Implants And Instrumentation" filed Feb. 24, 2010, the disclosure of which is incorporated herein by reference in its entirety.

As with the patient-specific feature(s) of an implant component or guide tool, the patient-engineered features of an implant component or guide tool can be designed (e.g., preoperatively designed and manufactured) or they can be selected, for example, by selecting an implant component that best meets the one or more predetermined parameters that enhance one or more features of the patient's biology.

Moreover, an implant component or guide tool can include a patient-engineered feature that is both selected and designed. For example, an implant component initially can be selected (e.g., preoperatively selected from a library of implants) to have a feature with a larger or smaller dimension than the desired patient-engineered dimension. Then, the implant component can be machined (if selected from an actual library of implant components) or manufactured (if selected from a virtual library of implant components) so that the larger-dimensioned or smaller-dimensioned implant feature is altered to have the desired patient-engineered dimension.

Implant Systems

As described herein, an implant (also referred to as an "implant system") can include one or more implant components, which, can each include one or more patient-specific features, one or more patient-engineered features, and one or more standard (e.g., off-the-shelf) features. Moreover, an implant system can include one or more patient-adapted (e.g., patient-specific and/or patient-engineered) implant components and one or more standard (i.e., non-patient-specific features) implant components.

For example, a knee implant can include a femoral implant component having one or more patient-adapted and standard features, and an off-the-shelf tibial implant component having only standard features. In this example, the entire tibial implant component can be off-the-shelf. Alternatively, a metal-backed implant component (or portion of an implant component) can be patient-specific, e.g., matched in the A-P dimension or the M-L dimension to the patient's tibial cortical bone, while the corresponding plastic insert implant component (or corresponding portion of the implant component) can include a standard off-the-shelf configuration.

Exemplary Implant Systems and Patient-Adapted Features

In certain embodiments described herein, an implant or implant system can include one, two, three, four or more components having one or more patient-specific features that substantially match one or more of the patient's biological features, for example, one or more dimensions and/or measurements of an anatomical/biological structure, such as bone, cartilage, tendon, or muscle; a distance or space between two or more aspects of a biological structure and/or between two or more different biological structures; and a biomechanical or kinematic quality or measurement of the patient's biology. In addition or alternatively, an implant component can include one or more features that are engineered to optimize or enhance one or more of the patient's biological features, for example, (1) deformity correction and limb alignment (2) preserving bone, cartilage, and/or ligaments, (3) preserving and/or optimizing other features of the patient's anatomy, such as trochlea and trochlear shape, (4) restoring and/or optimizing joint kinematics or biomechanics, and/or (5) restoring and/or optimizing joint-line location and/or joint gap width. In addition, an implant component can be designed and/or manufactured to include one or more standard (i.e., non-patient-adapted) features.

Exemplary patient-adapted (e.g., patient-specific and/or patient-engineered) features of the implant components described herein are identified in Table 1. One or more of these implant component features can be selected and/or designed based on patient-specific data, such as image data.

TABLE 1

Exemplary implant features that can be
patient-adapted based on patient-specific measurements

| Category | Exemplary feature |
|---|---|
| Implant or component (applies knee, shoulder, hip, ankle, or other implant or implant component) | One or more portions of, or all of, an external implant component curvature |
| | One or more portions of, or all of, an internal implant dimension |
| | One or more portions of, or all of, an internal or external implant angle |
| | Portions or all of one or more of the ML, AP, SI dimension of the internal and external component and component features |
| | An locking mechanism dimension between a plastic or non-metallic insert and a metal backing component in one or more dimensions |
| | Component height |
| | Component profile |
| | Component 2D or 3D shape |
| | Component volume |
| | Composite implant height |
| | Insert width |
| | Insert shape |
| | Insert length |
| | Insert height |
| | Insert profile |
| | Insert curvature |
| | Insert angle |
| | Distance between two curvatures or concavities |
| | Polyethylene or plastic width |
| | Polyethylene or plastic shape |
| | Polyethylene or plastic length |
| | Polyethylene or plastic height |
| | Polyethylene or plastic profile |
| | Polyethylene or plastic curvature |
| | Polyethylene or plastic angle |
| | Component stem width |
| | Component stem shape |
| | Component stem length |
| | Component stem height |
| | Component stem profile |
| | Component stem curvature |
| | Component stem position |
| | Component stem thickness |
| | Component stem angle |
| | Component peg width |
| | Component peg shape |
| | Component peg length |
| | Component peg height |
| | Component peg profile |
| | Component peg curvature |
| | Component peg position |
| | Component peg thickness |
| | Component peg angle |
| | Slope of an implant surface |
| | Number of sections, facets, or cuts on an implant surface |
| Femoral implant or implant component | Condylar distance of a femoral component, e.g., between femoral condyles |
| | A condylar coronal radius of a femoral component |
| | A condylar sagittal radius of a femoral component |
| Tibial implant or implant component | Slope of an implant surface |
| | Condylar distance, e.g., between tibial joint-facing surface concavities that engage femoral condyles |
| | Coronal curvature (e.g., one or more radii of curvature in the coronal plane) of one or both joint-facing surface concavities that engage each femoral condyle |
| | Sagittal curvature (e.g., one or more radii of curvature in the sagittal plane) of one or both joint-facing surface concavities that engage each femoral condyle |

The patient-adapted features described in Table 1 also can be applied to patient-adapted guide tools described herein.

The patient-adapted implant components and guide tools described herein can include any number of patient-specific features, patient-engineered features, and/or standard features.

Pre-Primary, Primary, and Revision Systems

Certain embodiments are directed to implants, guide tools, and/or related methods that can be used to provide to a patient a pre-primary procedure and/or a pre-primary implant such that a subsequent, replacement procedure can be performed with a second (and, optionally, a third, and optionally, a fourth) patient-adapted pre-primary implant or with a traditional primary implant. In certain embodiments, the pre-primary implant procedure can include 3, 4, 5, 6, 7, or more resection or surgical cuts to the patient's bone and the pre-primary implant can include on its corresponding bone-facing surface a matching number and orientation of bone-cut facets or surfaces.

In one illustrative embodiment, a first pre-primary joint-replacement procedure includes a patient-adapted implant component, guide tool, and/or related method. The patient-adapted implant component, guide tool, and/or related method can be preoperatively selected and/or designed from patient-specific data (which can come from current and/or historical patient-specific information), such as one or more images of the patient's joint, to include one or more features that are patient-specific or patient-engineered. The features (e.g., dimensions, shape, surface contours) of the first pre-primary implant and, optionally, patient-specific data (e.g., features of the patient's resected bone surfaces and features of the patient's contralateral joint) can be stored in a database, for example, as historical patient-specific information. When the first pre-primary implant fails, for example, due to bone loss or osteolysis or aseptic loosening at a later point in time (e.g., 15 years after the original implantation) a second implant can be implanted. For the second implant procedure, the amount of diseased bone can be assessed. If the amount of diseased bone to be resected is minimal, the patient-specific data can be used to select and/or design a second pre-primary procedure and/or a pre-primary implant. If the amount of diseased bone to be resected is substantial, a traditional primary procedure and a traditional implant can be employed.

Alternatively, certain embodiments are directed to implants, guide tools, and/or related methods that can be used to provide to a patient a primary procedure and/or a primary implant such that a subsequent replacement implant can be used as part of a traditional revision procedure. Certain embodiments are directed to implants, guide tools, and/or related methods that can be used to provide a patient-adapted revision implant. For example, following a traditional implant, a subsequent revision can include a patient-adapted procedure and/or a patient-adapted implant component as described herein.

FIG. 1 is a flow chart illustrating a process that includes selecting and/or designing a first patient-adapted implant, for example, a pre-primary implant. First, using the techniques described herein or those suitable and known in the art, measurements of the target joint are obtained 210. This step can be repeated multiple times, as desired. Optionally, a virtual model of the joint can be generated, for example, to determine proper joint alignment and the corresponding resection cuts and implant component features based on the determined proper alignment. This information can be collected and stored 212 in a database 213, for example, as historical patient-specific information, as described further below. Once measurements of the target joint are obtained and analyzed to determine resection cuts and patient-adapted implant features, the patient-adapted implant components can be selected 214 (e.g., selected from a virtual library and optionally manufactured without further design alteration 215, or selected from a physical library of implant components). Alternatively, or in addition, one or more implant components with best-fitting and/or optimized features can be selected 214 (e.g., from a library) and then further designed (e.g., designed and manufactured) 216. Alternatively or in addition, one or more implant components with best-fitting and/or optimized features can be designed (e.g., designed and manufactured) 218, 216 without an initial selection from a library. Using a virtual model to assess the selected or designed implant component(s), this process also can be repeated as desired (e.g., before one or more physical components are selected and/or generated). The information regarding the selected and/or designed implant component(s) can be collected and stored 220, 222 in a database 213, for example, as historical patient-specific information. Once a desired first patient-adapted implant component or set of implant components is obtained, a surgeon can prepare the implantation site and install the first implant 224. The information regarding preparation of the implantation site and implant installation can be collected and stored 226 in a database 213, for example, as historical patient-specific information. This can be achieved, for example, using post-operative imaging (e.g., x-ray, fluoroscopy, CT, and/or MRI) or measurements obtained using a surgical navigation system. In this way, the information associated with the first pre-primary implant component is available for use by a surgeon for subsequent implantation of a second pre-primary or a primary implant.

Figure 2:
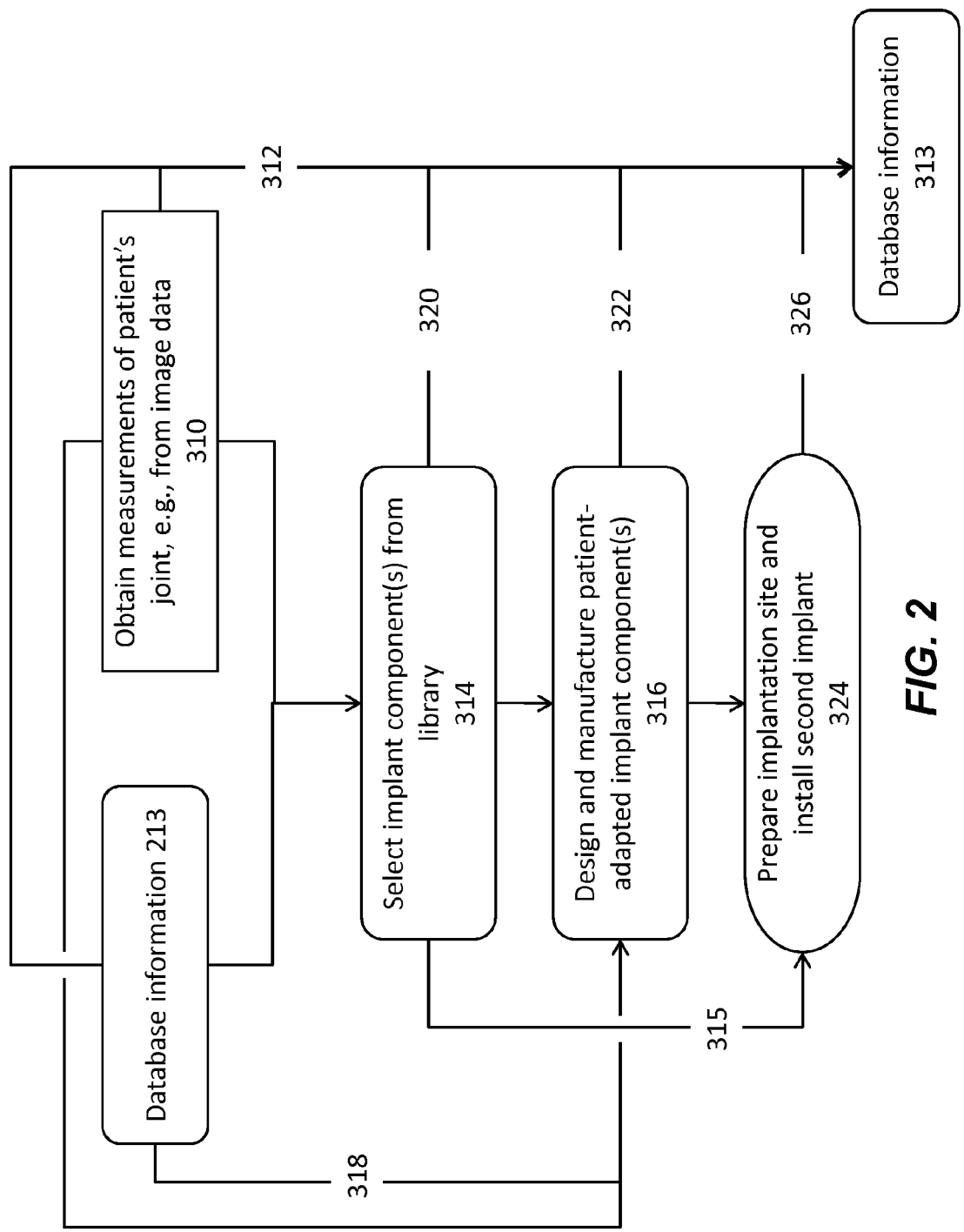
FIG. 2 is a flow chart illustrating a process that includes selecting and/or designing a second patient-adapted implant.

FIG. 2 is a flow chart illustrating a process that includes selecting and/or designing a second implant. In certain embodiments, the second implant can be a traditional primary implant. Alternatively, the second implant can be a patient-adapted implant, which optionally can be used as second pre-primary implant that allows for a subsequent (i.e., third) primary implant using a traditional implant.

The steps described in FIG. 2 are similar to those described above for a first pre-primary implant (see FIG. 1); however, in the second implant process, the database information 213, also referred to herein as historical patient-specific information, collected and stored in the first implant process can be used as part of the process for selecting and/or designing the second implant. In addition to the database information from the first implant process 213, additional measurements of the target joint optionally can be obtained 310 and used together with the database information 213 from the first implant process as a basis for selecting and/or designing a second implant. This step can be repeated multiple times, as desired. Optionally, a virtual model of the joint can be generated (with or without a model of the first implant), for example, to determine proper joint alignment, corresponding resection cuts and, optionally, patient-adapted implant component features based on the determined proper alignment. This information can be collected and stored 312 as new or additional database information 313 (e.g., historical patient-specific information). Once the database information from the first implant process and optionally new measurements of the target joint and first implant are obtained and analyzed, the implant component(s) for the second implant can be selected 314 (e.g., selected from a virtual library and optionally manufactured without further design alteration 315, or selected from a physical library of implant components, or selected from among traditional implant components). Alternatively or in addition, one or more implant components with best-fitting and/or optimized features can be selected 314 (e.g., from a library) and then further designed (e.g., designed and manufactured) 316. Alternatively or in addition, one or more implant components with best-fitting and/or optimized features can be designed (e.g., designed and manufactured) 038 without an initial selection from a library. Using a virtual model to assess the selected or designed implant component, this process also can be repeated as desired (e.g., before one or more physical components are selected and/or generated). The information regarding the selected and/or designed implant components for the second implant can be collected and stored 320, 322 in a database 313 (e.g., as historical patient-specific information). Once a desired implant component or set of implant components is obtained for the second implant, a surgeon can prepare the implantation site, including removing the first implant, and install the second implant 324. The information regarding preparation of the implantation site and second implant installation can be collected (e.g., using post-operative imaging (e.g., x-ray, fluoroscopy, CT, and/or MRI) or measurements obtained using a surgical navigation system) and stored 326 in a database 313 (e.g., as historical patient-specific information).

The second implant can have standard attachment mechanisms, e.g., a stem and or pegs or other attachment means known in the art. Alternatively, the attachment mechanisms can be patient-specific by deriving shape information on the residual bone, e.g., of a femur and acetabulum or of a femur and a tibia or of a humerus and a glenoid, using image data, e.g., CT or MRI data. One or more dimensions or shapes or joint-facing surfaces of the second implant can be adapted to include, at least in part, information reflective of the corresponding dimension(s) or shape(s) or joint-facing surface(s) of the first implant. In this manner, a better functional result can be achieved with the revision implant by maintaining patient-specific shapes and/or geometry in the revision implant by accessing data in the patient database.

Accordingly, certain embodiments described herein are directed to implants, implant components, guide tools, and related methods that address many of the problems associated with traditional implants, such as mismatches between an implant component and a patient's biological features (e.g., a feature of a biological structure, a distance or space between two biological structures, and/or a feature associated with anatomical function) and substantial bone removal that limits subsequent revisions following a traditional primary implant.

Figure 3:
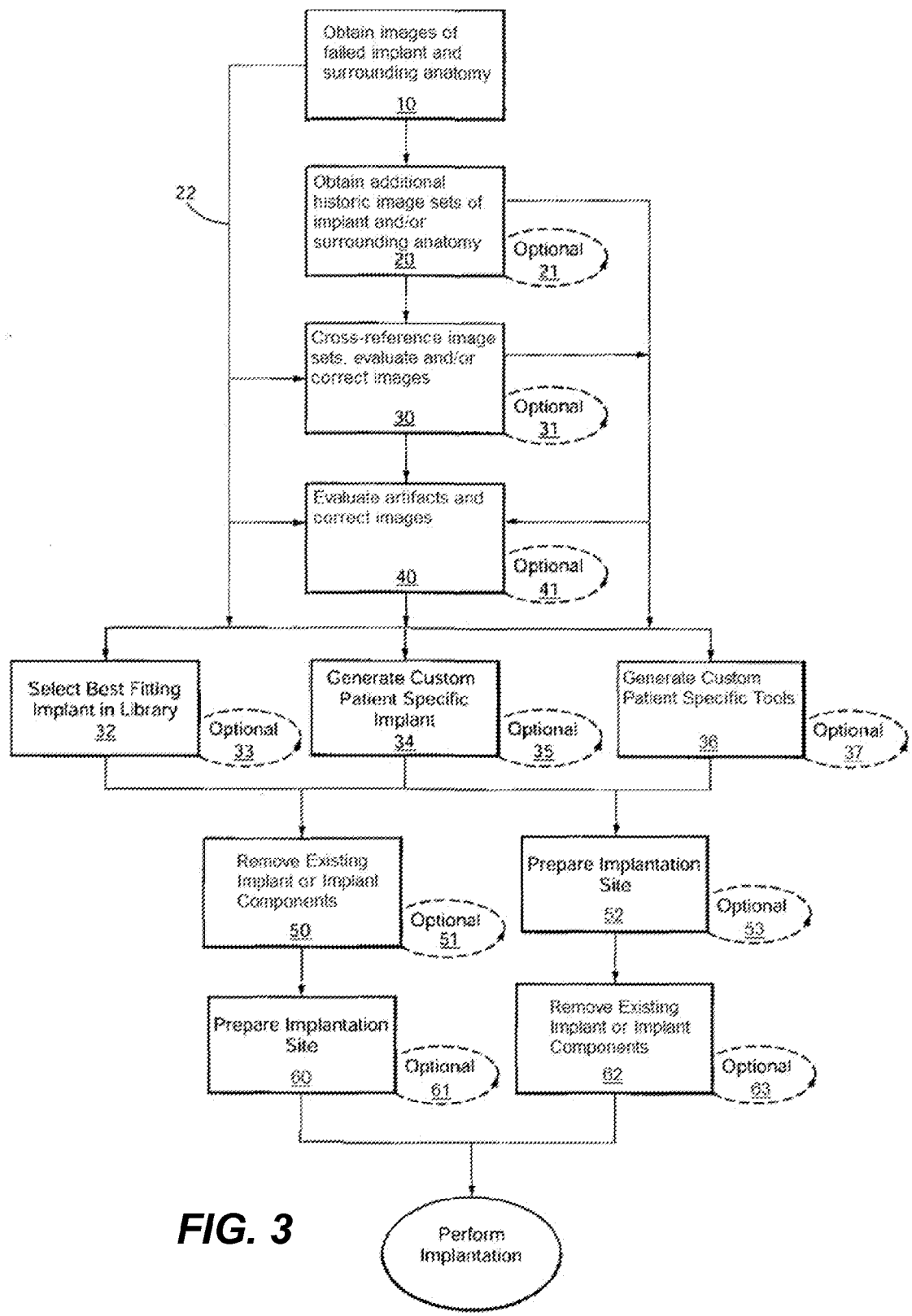
FIG. 3 is a flowchart illustrating methods of using multiple image sets for selecting and/or designing articular repair systems.
Figure 4:
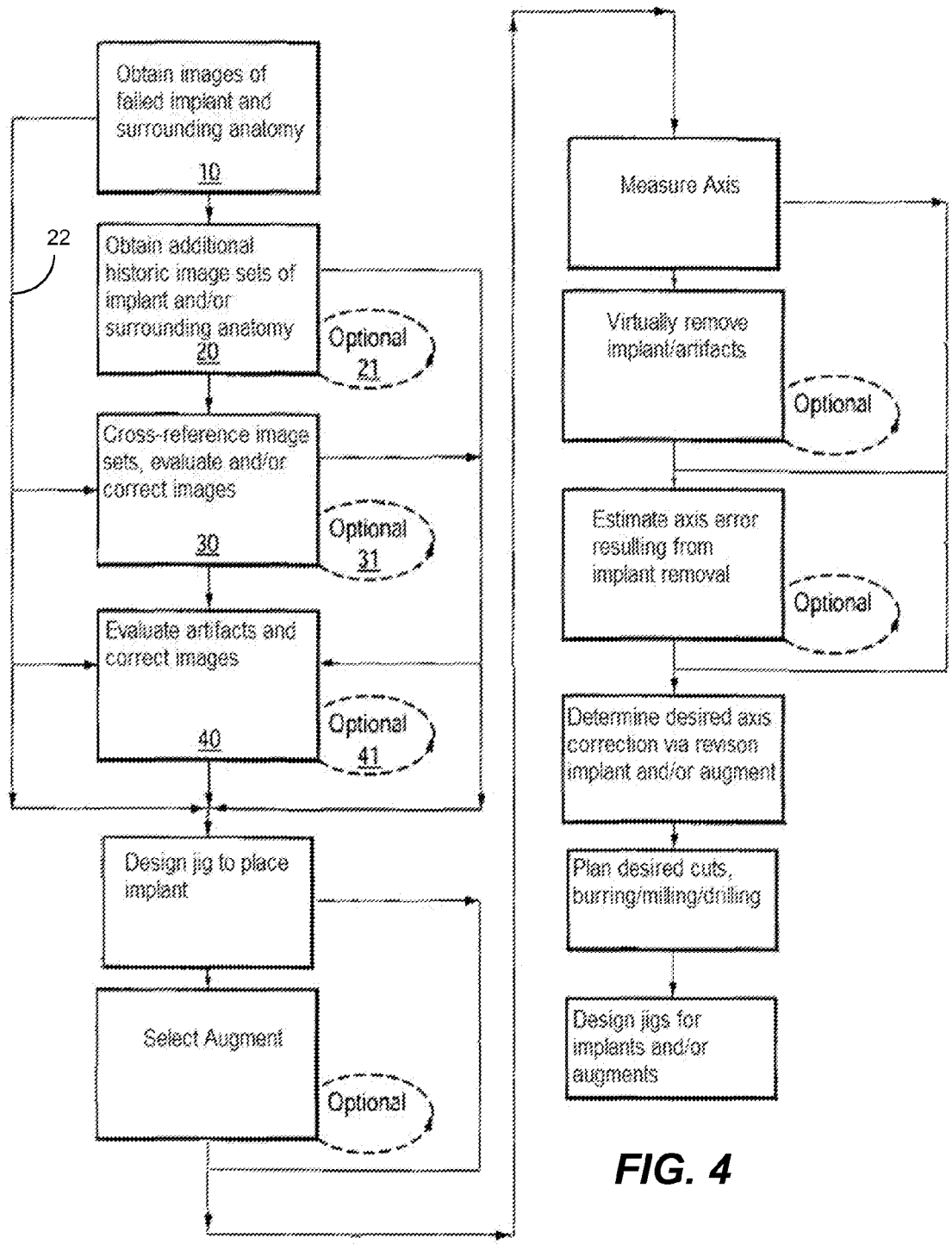
FIG. 4 is a flowchart illustrating methods of using multiple image sets for selecting and/or designing articular repair systems.

FIGS. 3 and 4 illustrate additional embodiments relating to replacing an existing implant with a revision implant. Such a process can begin by first obtaining one or more images of a patient's joint that requires revision (e.g., current patient-specific information). This group of images can typically have a series of images of the patient's current joint, which typically includes various images of the "failed" or "failing" implant (i.e., "failed implant" images). If available, the groups of images can also include other images taken earlier in the treatment progression of the failed joint (e.g., historical patient-specific information), including (1) images of the joint and/or implant taken between the time of original implantation and "failure" of the prior implant (i.e., "pre-failure implant" images), (2) images of the joint and/or implant taken at the time of original implantation (i.e., "initial implantation" images), (3) images taken prior to initial implantation of the "failed implant" (i.e., "pre-implant work-up" images), and (4) images taken prior to significant failure of the patient's natural joint (i.e., "healthy joint" images), and/or prior to any disease or damage of the joint.

Various additional image sources useful can include images of the "failed implant", both pre and post-failure (i.e., "implant data"), information or images regarding the types and locations of bone cement and/or bony in-growth structures, and any other anatomical data available regarding the patient, including resection surface information, residual cartilage, osteophytes, osteolysis, and/or information regarding injuries or disease states that may affect joint and/or bone strength in any manner (e.g., osteoporosis, arthritis). Where such additional image groups are readily available, it may be desirable to include such information in the current image group. Other sources of information could include databases of non-patient individuals (e.g., information from specific or general individuals, including normalized information, from specific or general population groups).

Table 2 provides a non-exhaustive list of various data sources and image characteristics potentially useful:

TABLE 2

Exemplary Sources of Imaging Data
Image sources

Current scan of patient's anatomy, including "failed implant" and/or "failed anatomy"
Time-lapse images or 4D images and motion studies of "failed implant"
Contrast enhanced studies of "failed implant"
Historical scans of patient's healthy joint currently requiring revision
Historical scans of patient's joint prior to implantation of "failed implant" (pre-failure)
Scans of patients contra-lateral (opposing) healthy joint
Scans and/or databases of healthy individuals and/or "matched" individuals from general population(s)
Historical scans of "failed implant" after initial implantation but pre-failure
Images and/or data regarding shape, size and features/configuration of "failed implant" (pre-implantation as well as "follow-up" images and image series)
Images and/or data regarding locations of bone cement of other non-biologic structures (i.e., anchors, pins, other implants, etc.)
Images and/or data regarding resection surfaces, unresected surfaces, residual cartilage, osteophytes, osteolysis, bone cement, or other anatomical features prior to implantation of the "failed implant"
Images or data or templates of implant components of "failed implant", either obtained in vivo in the patient or, for example, based on manufacturer's data, in 2D and 3D, including CAD files or other electronic files At any point in the various disclosed embodiments, the quality and reliability of various images may be assessed for accuracy, completeness, and/or optionally "normalized" to a set standard or standards to facilitate their use during subsequent steps of the disclosed embodiments. It is desirable that images of poor quality and/or low accuracy will optionally be identified and, if of lesser utility, given a rating of "low confidence" and/or discarded. In a similar manner, higher quality images and/or those of better accuracy may be given a "higher confidence" rating. If desired, images may be processed and/or enhanced to improve the usefulness of data contained therein, in a known manner.

Optionally, the various images in the image group may be evaluated and/or assessed or "cross-referenced" against one another. For example, it may be advantageous to compare, contrast and evaluate the various anatomical image groups over time (e.g., healthy joint, initial implantation, pre-failure implant, and/or failed implant images) to determine disease progression and/or estimate future disease progression. In a similar manner, it may be advantageous to compare, contrast and evaluate the various implant image groups over time (e.g., initial implantation, pre-failure implant, and/or failed implant images) to determine and/or identify implant failure modes (e.g., implant fracture, unacceptable or uneven wear zones, dislocation, modular failures, etc.) or underlying anatomical failure modes (e.g., underlying support structure failure, soft tissue disease, kinematic imbalances, tissue scarification, metastatic disease or infection, etc.).

"Cross-Referencing" of images in the context of the current disclosure contemplates the comparison of one image to another image in the same or a different group of images. Optionally, the "cross-referenced" images will have a common anatomical or other reference feature which facilitates the comparison of features between the relevant images. Cross-referencing can be in 2D and/or 3D; 2D data can be cross-referenced against 3D data. Historical data (e.g., historical patient-specific information) can be cross-referenced against current data. Such cross-referencing and comparison can be between images, as well as between individual anatomical features of each image against other anatomical features in the same image and/or against similar features from other images.

In addition, information from one set of images may be utilized in comparison with other images to identify inaccuracies or discrepancies across images and/or among image groups, which may decrease confidence in the accuracy of some images and/or identify additional areas of anatomical concern (e.g., implant fracture and/or dislocation). In a similar manner, information from one set of images may be utilized in comparison with other images to identify consistencies and/or congruencies across images, which may increase confidence in the accuracy of the various images (and/or image components, features or areas of interest) and/or identify anatomical and/or implant areas that remain unchanged or "not of concern" over time. The various accuracies and inaccuracies may be rated and identified in various ways, including through the use of a "heat map" or "color chart" that provides a 2-D, 3-D or 4-D (e.g., time-lapse or other such presentation) rendering of the anatomy and implant, with areas of high confidence in "cool" colors (e.g., blue and green) and areas of low confidence in "hot colors" (e.g., yellow and red) corresponding to various comparison factors, such as (1) significant changes in anatomy, (2) significant changes in implant characteristics and/or alignment, (3) significant perceived inaccuracies across image series, and (4) significant areas or scarification, bone remodeling, etc. Various embodiments may display and/or identify areas of estimated anatomical margins and/or implant location as a "confidence contour map" or other display.

Another advantage for conducting comparisons across image series could include identifying and/or correcting imaging inaccuracies caused or induced by "artifacts" or other factors during the imaging process. For example, metallic "artifacts" (including metallic joint replacement implants) are known to affect the quality of some non-invasive image methods (e.g., x-ray, CT, MRI, etc.) to various degrees, especially where the "location of interest" is adjacent to the artifacts. Not only can such artifacts mask the anatomy near such objects, but such artifacts may cause significant image distortion, which significantly reduces the utility of such imaging in planning and assessing anatomical structures during revision procedures. If desired, artifact reduction algorithms or other processing steps (including enhancement of low-metal artifact information), as well as imaging techniques optionally "less sensitive" to artifact distortion, may be utilized in an attempt to improve image quality and/or reliability. In addition, the use and comparison of multiple images of the same anatomical region and/or implant, utilizing differing imaging methods (to optionally highlight different types and/or portions of anatomy and/or implant) are contemplated in various embodiments. The use of other images in the image series, including images taken prior to initial implantation of the "artifact," can be used to cross-check the accuracy of such artifact-laden images, and may also be used to correct such distortion where applicable. In a similar manner, data regarding the structure of the "failed implant" may be especially useful in such situations. The external margins of the "failed implant" are often readily discernible on non-invasive images, and knowledge of the internal and peripheral features of the implant (e.g., implant design, shape and size, including bone-facing surfaces of the implant) can be calculated and/or cross-referenced from or against the external margins to estimate the location of corresponding internal surfaces (which are optionally adjacent to estimated margins of the anatomical support structures). Moreover, knowledge of the internal surface location can be used to cross-reference against other images, including against other images of the same implant from differing angles, as well as can be used to identify limits or locations where anatomical structures can or cannot be. Any image that identifies an anatomical structure within a location where the implant exists (e.g., anatomy and implant structure at the same 3-dimensional location) should be either incorrect or may indicate a fractured, dislocated or otherwise displaced implant. Information regarding the thicknesses of implant material at various locations or along various planes may also be useful in evaluating the amount of distortion experienced in a given image or portion of image. Similar implant data can be utilized to determine the thickness of a metal implant along various planes of imaging, and may be utilized to estimate the amount of implant distortion experienced as well as to identify "preferred" imaging angle to reduce or minimize distortion (e.g., choose imaging planes to minimize implant thickness, or to place known planar implant surfaces perpendicular to x-ray imaging).

Information about the 2-dimensional and/or 3-dimensional shape of the implant can also be used for cross-referencing of different image sets. For example, the image representation of the implant shown in both image sets can be matched, which allows for co-registration of both image sets into the same coordinate system.

In some exemplary embodiments, the use of images from a prior scan of the patient (e.g., historical patient-specific information), in combination with a current scan (e.g., current patient-specific information) of the patient (containing failed implant image(s)) and known data regarding the shape and size of the failed implant (including internal and external surface dimensions) can be processed and/or utilized to provide significant useful data regarding the quality and quantity of anatomical support structure available for use with a revision implant procedure. By knowing the amount of potential anatomical support structure remaining, this embodiment allows the revision implant to be selected and/or designed to require minimum resection and/or preparation of remaining anatomical support structures after implant removal. In addition, if the implant has fractured or otherwise failed in a manner whereby the anatomical support structure has remained substantially intact, a replacement (revision) implant can be chosen or designed that requires little or no alteration to the underlying anatomical support structure prior to implantation. If desired, the bone-facing structures of the revision implant can replicate those of the "failed implant" (to facilitate implantation with little or no cutting or preparation of the underlying anatomical surfaces), while alterations to the joint-facing or articulating structures (and/or the thickness of the implant) can alter the biomechanics of the revision implant and revised joint in a desirable manner.

Another alternate embodiment could utilize the original scans (e.g., historical patient-specific information) of the patient's anatomy (either prior to or after initial implantation of the primary implant) to create a revision implant and/or surgical tools for use in preparing the anatomical support surfaces for the revision implant. Such devices could include patient-specific anatomical support surfaces for alignment and/or placement of the revision implant. If desired, the original scan data could be normalized, assessed, evaluated and/or corrected as described herein to improve image accuracy and/or quality.

TABLE 3

Exemplary Anatomical and Implant Features

| Anatomical Features | Implant Features |
|---|---|
| Resection surfaces of bone due to primary implant | Internal (bone facing) surfaces of the "failed implant" |
| Unresected bone surfaces | Chamfer cut dimensions and locations of the "failed implant," e.g. based on image data or manufacturer data, in 2D or 3D |
| Residual cartilage | |
| Osteophytes | |
| Osteolysis | External (joint facing) surfaces of the "failed implant," e.g. based on image data or manufacturer data, in 2D or 3D |
| Bone Cement | |
| Bone density | |
| Bone structure | Surface corners |
| | Peripheral edge(s) |
| | Notches |
| | Stem shape of the "failed implant," e.g. based on image data or manufacturer data, in 2D or 3D |
| | Insert shape, e.g. polyethylene, of the "failed implant," e.g. based on image data (e.g. actual) or manufacturer data (e.g. prior to failure), in 2D or 3D |

In a similar manner, the images may be corrected or otherwise evaluated for accuracies relevant to the type and size/thickness of the implant, other artifact, or general or specific known or unknown inaccuracies in the imaging equipment and/or modality. For example, areas of high metal concentration (e.g., thicker sections of an implant) may be more prone to artifact distortion than areas of lesser metal concentration. Similarly, various metal types may be more or less prone to artifact distortion, as will artifacts having low-metal content such as some ceramics and polymers. In addition, the different types of imaging equipment are likely to have different accuracies, not only due to the differing imaging modalities (e.g., 2-D vs. 3D vs. 4D imaging, MRI, CT-scan, CAT, fluoroscopy and x-ray, ultrasound, PET, and/or other radiographic, nuclear, photo-acoustic, thermographic, tomographic and/or ultrasonic imaging techniques, etc.), but also calibration of the related equipment, age of the scans (e.g., older scans may have been held to a lower accuracy standard or may have degraded in storage), and inherent differences in the equipment and/or the various environments of use (e.g., heat, temperature, etc). All or some of these various factors may be included with image data to increase, decrease or otherwise assess the "confidence" of the data accuracy, which may affect how such data is viewed and/or rated during assessment, evaluation, comparison/cross-referencing and/or correction of some of all of the image data. For example, where an older image depicts an anatomical feature that does not correlate to more recent image groups, the older image data may be considered "less reliable" than newer image data, and may be appropriately assessed (e.g., discarded or assigned a low reliability value)

or alternatively may be judged to be "more reliable" where the older image was taken without artifact interference, or by a more reliable imaging modality, etc. Each image or image group (including individual features of interest within an image) may, if desired, be assigned such "reliability ratings," or individual features of images may have differing "reliability ratings", or combinations thereof. The assessment system may also identify common anatomical features across differing image groups, which may affect "reliability ratings" in either a positive or negative manner.

The present disclosure contemplates a wide variety of "priority" or "ranking" systems for use with the various assessment and evaluation systems of the present disclosure. Virtually any combination of priorities can be incorporated into the assessment and evaluation process, typically on a user-defined basis, although the use of pre-defined priorities and/or groups of priorities is also encompassed by this disclosure. For example, higher priorities may be given to data assessed as having a greater "likelihood of accuracy" as defined by the user and/or system. Such greater likelihood could be due to a wide variety of factors, including (1) inherent accuracy of the imaging method, (2) multiple groups of images identifying a common anatomical feature or features (and/or "failed implant" feature or features) in the same or similar location, and/or (3) images where artifacts are absent or have been corrected for. Similarly, the evaluation process can include varying priorities as defined by the user or others, including (1) cost priorities for selecting and/or designing an implant in the most cost-efficient (or least-cost efficient or any variations thereof) manner (e.g., manufacturing costs, material costs, processing/machining costs, use of pre-existing implants versus custom built implants, etc.), (2) scheduling or availability priorities for selecting and/or designing an implant in the time-efficient (or least-time efficient or any variations thereof) manner (e.g., to ensure an implant will be available for use within a specified time frame, etc.), and/or (3) inventory management issues (e.g., to utilize materials and/or implant sizes that are already manufactured and/or are being manufactured in larger quantities, etc).

Once the images have, optionally, been compared, evaluated, cross-referenced and/or normalized, one or more composite image sets or output sets or generated images may be produced that optionally reflect one or more of the following (1) the most accurate and correct image or set of images of the failed implant, (2) the most accurate and complete image or set of images of the underlying anatomical support structure(s), and/or (3) one or more images or "boundary diagrams" of the anatomical support structures that are estimated to remain after removal of the failed implant. This information may then be used to create revision implants and surgical tools particularized for use in removing the failed implant, revising the supporting anatomical structures, and implanting the revision implant in a desired fashion. Such information may also assist in evaluating and assessing the patient's disease state and/or progression of disease and/or degeneration over a period of time.

If desired, various embodiments may include a graphical user interface (GUI) that allows an operator (surgeon, implant designer, patient, etc.) to conduct pre-operative planning of the revision procedure, including simulating post-operative alignment of the revision implant incorporating augments and/or spacers, wherein the spacer and/or augment can be selected by the user and the alignment information and possible surface information can be modeled, displayed and/or built into (or otherwise incorporated into) the surgical tools and/or surgical implant, including jigs or guides that the jigs include.

In various embodiments, an exterior surface model or "frame diagram" of the failed implant and surrounding anatomical structure of the joint can be created electronically (and/or physically, if desired). In a manner similar to the creation of implants and/or surgical tools and molds described previously in various embodiments of this disclosure, portions of the frame diagram (or physical model) may be utilized to create conforming surfaces for engagement by the surgical tools and molds (e.g., utilizing only surface features of the failed implant, using surface features of the failed implant in combination with anatomical features of the joint surfaces and/or using only anatomical features of the joint surfaces to align the tools and/or molds). Similarly, portions of the frame diagram (or physical model) may be utilized to design and/or select the interior and/or exterior surfaces of the revision implant.

It may also be desirous for an evaluation system to have the capability of evaluating the type and/or size of failed implant in various image sets, including the capability to identify unidentified implants or implant components (and possibly verify the identity of a known or suspected implant type) from a database of known implant designs. In many cases, the exact design, shape and/or size of the failed implant will be unknown, either because surgical records are unavailable, are disorganized or are incorrect, and the use of proper implant information may be important to the evaluation and assessment of various patient information. In various embodiments, the system is optionally capable of evaluation the condition of various implants and/or implant components, facilitating identification of failed or fractured components that may require replacement, while the remaining components may remain in situ, as desired. Once identified, information and/or data regarding the various implant components can be included in the various image/data groups for assessment and/or evaluation and preparation of the revision implant and/or tools. Of course, if information regarding the "failed implant" is already known or is available, such implant information (possibly available based on patient history, surgical reports and/or manufacturer's records) may be included, utilized and/or verified by the evaluation system.

Once the processing, assessment, evaluation and/or cross-referencing/correcting of patient and "failed implant" information has been accomplished to a desired degree, the resulting image and/or data information may be utilized to plan the revision surgery, which can include the creation of revision implants, implant components and surgical tools for preparation of anatomical surfaces and implantation of the revision implant. Revision surgery is particularly well suited to the systems and methods described herein, as the disclosed methods are capable of determining and/or estimating the patient's anatomical structure underlying the "failed implant" to a degree significantly greater than that allowed by current practice. For example, in a typical knee revision procedure, a physician is often unaware of the actual structure and/or condition of the underling margins of the anatomical support structure (e.g., bone and any remaining articular surfaces that may have supported the "failed implant") until the failed implant has been removed in surgery. Because of this, revision implants typically plan and are designed for significant bone removal (to accommodate a "worst case" scenario where most supporting bone has degraded), and often also require an intramedullary stem that serves as an alignment structure for aligning the joint implant, as well as a support structure for securing the implant to the surrounding bone. With the disclosed system, however, a more accurate estimate of the underlying bony support structure can be determined, and thus less bone and other support structures need be removed in preparing for the revision implant, as well as allowing for a revision implant or implant components to be constructed appropriate to the existing support structure. In addition, the identification of existing support structures, in combination with the use of the failed implant as an anatomical reference point, allows positioning of the revision implant without necessarily resorting to intramedullary or other highly-invasive reference points or methods. Moreover, the present method enables a surgeon to determine, prior to surgery, whether sufficient anatomical support structures remain to support the revision implant without need for an intramedullary stem or other such support structure.

If desired, an appropriate revision implant can be selected from a library or a revision implant can be generated based on the patient specific parameters obtained in the measurements and evaluation. If desired, surgical tools such as custom jigs to assist in the preparation of the anatomical surface can be constructed using information regarding the implant as well as the generated image data. Prior to installing the implant in the joint, the implantation site is prepared and then the implant is installed. One or more of these steps can be repeated as necessary or desired as shown by the optional repeat steps. In various embodiments, the surgical tools of the present disclosure can be particularized for use in a patient, for the implantation of a standard joint replacement implant (i.e., a standard or non-patient-specific implant), as desired.

In various embodiments, the resulting image and/or data information may be utilized to create a "custom" revision implant well suited to match and/or conform to the most accurate anatomical data. In various additional embodiments, the resulting data and/or image information may be utilized in combination with "confidence" or "statistical accuracy" data derived by the evaluation software to a degree defined by the user. For example, an implant and/or surgical tool may be specifically designed to have a "95%" confidence that the implant/surgical tool will fit the derived anatomical structure, and would thus be designed such that the internal structural surfaces would accommodate, encompass and/or conform to an anatomical model that follows the estimated contours of the underlying anatomical structures to at least a 95% confidence level. If desired, multiple implants of various confidence levels may be produced for use in a single surgery, with an implant of relatively "lower" confidence value being designed for a patient-specific application for use in a manner similar to a "rescue" revision implant where actual bone conditions significantly different from those estimated, or if the primary revision implant will not accommodate or properly fit the actual anatomical surfaces.

Collecting and Modeling Patient-Specific Information

As mentioned above, certain embodiments include implant components designed and made using patient-specific information that is collected preoperatively. The patient-specific data can include points, surfaces, and/or landmarks, collectively referred to herein as "reference points." In certain embodiments, the reference points can be selected and used to derive a varied or altered surface, such as, without limitation, an ideal surface or structure. For example, the reference points can be used to create a model of the patient's relevant biological feature(s) and/or one or more patient-adapted surgical steps, tools, and implant components. For example the reference points can be used to design a patient-adapted implant component having at least one patient-specific or patient-engineered feature, such as a surface, dimension, or other feature.

Sets of reference points can be grouped to form reference structures used to create a model of a joint and/or an implant design. Designed implant surfaces can be derived from single reference points, triangles, polygons, or more complex surfaces, such as parametric or subdivision surfaces, or models of joint material, such as, for example, articular cartilage, subchondral bone, cortical bone, endosteal bone or bone marrow. Various reference points and reference structures can be selected and manipulated to derive a varied or altered surface, such as, without limitation, an ideal surface or structure.

The reference points can be located on or in the joint that will receive the patient-specific implant. For example, the reference points can include weight-bearing surfaces or locations in or on the joint, a cortex in the joint, and/or an endosteal surface of the joint. The reference points also can include surfaces or locations outside of but related to the joint. Specifically, reference points can include surfaces or locations functionally related to the joint. For example, in embodiments directed to the knee joint, reference points can include one or more locations ranging from the hip down to the ankle or foot. The reference points also can include surfaces or locations homologous to the joint receiving the implant. For example, in embodiments directed to a knee, a hip, or a shoulder joint, reference points can include one or more surfaces or locations from the contralateral knee, hip, or shoulder joint.

Measuring Biological Features

Reference points and/or data for obtaining measurements of a patient's joint, for example, relative-position measurements, length or distance measurements, curvature measurements, surface contour measurements, thickness measurements (in one location or across a surface), volume measurements (filled or empty volume), density measurements, and other measurements, can be obtained using any suitable technique. For example, one dimensional, two-dimensional, and/or three-dimensional measurements can be obtained using data collected from mechanical means, laser devices, electromagnetic or optical tracking systems, molds, materials applied to the articular surface that harden as a negative match of the surface contour, and/or one or more imaging techniques described above and/or known in the art. Data and measurements can be obtained non-invasively and/or preoperatively. Alternatively, measurements can be obtained intraoperatively, for example, using a probe or other surgical device during surgery.

In certain embodiments, imaging data collected from the patient, for example, imaging data from one or more of x-ray imaging, digital tomosynthesis, cone beam CT, non-spiral or spiral CT, non-isotropic or isotropic MRI, SPECT, PET, ultrasound, laser imaging, photo-acoustic imaging, is used to qualitatively and/or quantitatively measure one or more of a patient's biological features, one or more of normal cartilage, diseased cartilage, a cartilage defect, an area of denuded cartilage, subchondral bone, cortical bone, endosteal bone, bone marrow, a ligament, a ligament attachment or origin, menisci, labrum, a joint capsule, articular structures, and/or voids or spaces between or within any of these structures. The qualitatively and/or quantitatively measured biological features can include, but are not limited to, one or more of length, width, height, depth and/or thickness; curvature, for example, curvature in two dimensions (e.g., curvature in or projected onto a plane), curvature in three dimensions, and/or a radius or radii of curvature; shape, for example, two-dimensional shape or three-dimensional shape; area, for example, surface area and/or surface contour; perimeter shape; and/or volume of, for example, the patient's cartilage, bone (subchondral bone, cortical bone, endosteal bone, and/or other bone), ligament, and/or voids or spaces between them.

In certain embodiments, measurements of biological features can include any one or more of the illustrative measurements identified in Table 4.

TABLE 4

Exemplary patient-specific measurements of biological features that can be used in the creation of a model and/or in the selection and/or design of an implant component

| Anatomical feature | Exemplary measurement |
|---|---|
| Joint-line, joint gap | Location relative to proximal reference point |
| | Location relative to distal reference point |
| | Angle |
| | Gap distance between opposing surfaces in one or more locations |
| | Location, angle, and/or distance relative to contralateral joint |
| Soft tissue tension and/or balance | Joint gap distance |
| | Joint gap differential, e.g., medial to lateral |
| Medullary cavity | Shape in one or more dimensions |
| | Shape in one or more locations |
| | Diameter of cavity |
| | Volume of cavity |
| Subchondral bone | Shape in one or more dimensions |
| | Shape in one or more locations |
| | Thickness in one or more dimensions |
| | Thickness in one or more locations |
| | Angle, e.g., resection cut angle |
| Cortical bone | Shape in one or more dimensions |
| | Shape in one or more locations |
| | Thickness in one or more dimensions |
| | Thickness in one or more locations |
| | Angle, e.g., resection cut angle |
| | Portions or all of cortical bone perimeter at an intended resection level |
| Endosteal bone | Shape in one or more dimensions |
| | Shape in one or more locations |
| | Thickness in one or more dimensions |
| | Thickness in one or more locations |
| | Angle, e.g., resection cut angle |
| Cartilage | Shape in one or more dimensions |
| | Shape in one or more locations |
| | Thickness in one or more dimensions |
| | Thickness in one or more locations |
| | Angle, e.g., resection cut angle |
| Intercondylar notch | Shape in one or more dimensions |
| | Location |
| | Height in one or more locations |
| | Width in one or more locations |
| | Depth in one or more locations |
| | Angle, e.g., resection cut angle |
| Medial condyle | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Lateral condyle | 2D and/or 3D shape of a portion or all |
| | Height in one or more locations |
| | Length in one or more locations |
| | Width in one or more locations |
| | Depth in one or more locations |
| | Thickness in one or more locations |

TABLE 4-continued

Exemplary patient-specific measurements of biological features that can be used in the creation of a model and/or in the selection and/or design of an implant component

| Anatomical feature | Exemplary measurement |
|---|---|
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Trochlea | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Groove location in one or more locations |
| | Trochlear angle, e.g. groove angle in one or more locations |
| | Slope in one or more locations and/or directions |
| | Angle, e.g., resection cut angle |
| | Portions or all of cortical bone perimeter at an intended resection level |
| | Resection surface at an intended resection level |
| Medial trochlea | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Central trochlea | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Groove location in one or more locations |
| | Trochlear angle, e.g. groove angle in one or more locations |
| | Slope in one or more locations and/or directions |
| | Angle, e.g., resection cut angle |
| | Portions or all of cortical bone perimeter at an intended resection level |
| | Resection surface at an intended resection level |
| Lateral trochlea | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Entire tibia | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions (e.g. medial and/or lateral) |

TABLE 4-continued

Exemplary patient-specific measurements of biological features that can be used in the creation of a model and/or in the selection and/or design of an implant component

| Anatomical feature | Exemplary measurement |
|---|---|
| | Angle, e.g., resection cut angle |
| | Axes, e.g., A-P and/or M-L axes |
| | Osteophytes |
| | Plateau slope(s), e.g., relative slopes medial and lateral |
| | Plateau heights(s), e.g., relative heights medial and lateral |
| | Bearing surface radii, e.g., relative radii medial and lateral |
| | Perimeter profile |
| | Portions or all of cortical bone perimeter at an intended resection level |
| | Resection surface at an intended resection level |
| Medial tibia | 2D and/or 3D shape of a portion or all |
| | Height in one or more locations |
| | Length in one or more locations |
| | Width in one or more locations |
| | Depth in one or more locations |
| | Thickness or height in one or more locations |
| | Curvature in one or more locations |
| | Slope in one or more locations and/or directions |
| | Angle, e.g., resection cut angle |
| | Perimeter profile |
| | Portions or all of cortical bone perimeter at an intended resection level |
| | Resection surface at an intended resection level |
| Lateral tibia | 2D and/or 3D shape of a portion or all |
| | Height in one or more locations |
| | Length in one or more locations |
| | Width in one or more locations |
| | Depth in one or more locations |
| | Thickness/height in one or more locations |
| | Curvature in one or more locations |
| | Slope in one or more locations and/or directions |
| | Angle, e.g., resection cut angle |
| | Perimeter profile |
| | Portions or all of cortical bone perimeter at an intended resection level |
| | Resection surface at an intended resection level |
| Entire patella | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Perimeter profile |
| | Angle, e.g., resection cut angle |
| | Portions or all of cortical bone perimeter at an intended resection level |
| | Resection surface at an intended resection level |
| Medial patella | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Central patella | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Lateral patella | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Femoral head | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Anteversion or retroversion |
| | Portions or all of bone perimeter at an intended resection level |
| | Resection surface at an intended resection level |
| Femoral neck | 2D and/or 3D shape of a portion or all |
| | Height in one or more locations |
| | Length in one or more locations |
| | Width in one or more locations |
| | Depth in one or more locations |
| | Thickness in one or more locations |
| | Angle in one or more locations |
| | Neck axis in one or more locations |
| | Curvature in one or more locations |
| | Slope in one or more locations and/or directions |
| | Angle, e.g., resection cut angle |
| | Anteversion or retroversion |
| | Leg length |
| | Portions or all of cortical bone perimeter at an intended resection level |
| | Resection surface at an intended resection level |
| Femoral shaft | 2D and/or 3D shape of a portion or all |
| | Height in one or more locations |
| | Length in one or more locations |
| | Width in one or more locations |
| | Depth in one or more locations |
| | Thickness in one or more locations |
| | Angle in one or more locations |
| | Shaft axis in one or more locations |
| | Curvature in one or more locations |
| | Angle, e.g., resection cut angle |
| | Anteversion or retroversion |
| | Leg length |
| | Portions or all of cortical bone perimeter at an intended resection level |
| | Resection surface at an intended resection level |
| Acetabulum | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Anteversion or retroversion |
| | Portions or all of cortical bone perimeter at an intended resection level |

TABLE 4-continued

Exemplary patient-specific measurements of biological features that can be used in the creation of a model and/or in the selection and/or design of an implant component

| Anatomical feature | Exemplary measurement |
|---|---|
| Glenoid | Resection surface at an intended resection level |
| | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Anteversion or retroversion |
| | Portions or all of cortical bone perimeter at an intended resection level |
| | Resection surface at an intended resection level |
| Humeral head | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Anteversion or retroversion |
| | Portions or all of cortical bone perimeter at an intended resection level |
| | Resection surface at an intended resection level |
| Humeral neck | 2D and/or 3D shape of a portion or all |
| | Height in one or more locations |
| | Length in one or more locations |
| | Width in one or more locations |
| | Depth in one or more locations |
| | Thickness in one or more locations |
| | Angle in one or more locations |
| | Neck axis in one or more locations |
| | Curvature in one or more locations |
| | Slope in one or more locations and/or directions |
| | Angle, e.g., resection cut angle |
| | Anteversion or retroversion |
| | Arm length |
| | Portions or all of cortical bone perimeter at an intended resection level |
| | Resection surface at an intended resection level |
| Humeral shaft | 2D and/or 3D shape of a portion or all |
| | Height in one or more locations |
| | Length in one or more locations |
| | Width in one or more locations |
| | Depth in one or more locations |
| | Thickness in one or more locations |
| | Angle in one or more locations |
| | Shaft axis in one or more locations |
| | Curvature in one or more locations |
| | Angle, e.g., resection cut angle |
| | Anteversion or retroversion |
| | Arm length |
| | Portions or all of cortical bone perimeter at an intended resection level |
| | Resection surface at an intended resection level |
| Ankle joint | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Elbow | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Wrist | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Hand | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Finger | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle |
| | Portions or all of cortical bone perimeter at an intended resection level |
| | Resection surface at an intended resection level |
| Spine | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Spinal facet joint | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |

Depending on the clinical application, a single or any combination or all of the measurements described in Table 4 and/or known in the art can be used. Additional patient-specific measurements and information that be used in the evaluation can include, for example, joint kinematic measurements, bone density measurements, bone porosity measurements, identification of damaged or deformed tissues or structures, and patient information, such as patient age, weight, gender, ethnicity, activity level, and overall health status. Moreover, the patient-specific measurements may be compared, analyzed of otherwise modified based on one or more "normalized" patient model or models, by reference to a desired database of anatomical features of interest, and/or by reference to historical patient-specific information. For example, a series of patient-specific femoral measurements may be compiled and compared to one or more exemplary femoral or tibial measurements from a library or other database of "normal" femur measurements. Comparisons and analysis thereof may concern, but is not limited to one, more or any combination of the following dimensions: femoral shape, length, width, height, of one or both condyles, intercondylar shapes and dimensions, trochlea shape and dimensions, coronal curvature, sagittal curvature, cortical/cancellous bone volume and/or quality, etc., and a series of recommendations and/or modifications may be accomplished. Any parameter mentioned in the specification and in the various Tables throughout the specification including anatomic, biomechanical and kinematic parameters can be utilized, not only in the knee, but also in the hip, shoulder, ankle, elbow, wrist, spine and other joints. Such analysis may include modification of one or more patient-specific features and/or design criteria for the implant to account for any underlying deformity reflected in the patient-specific measurements. If desired, the modified data may then be utilized to choose or design an appropriate implant to match the modified features, and a final verification operation may be accomplished to ensure the chosen implant is acceptable and appropriate to the original unmodified patient-specific measurements (i.e., the chosen implant will ultimately "fit" the original patient anatomy). In alternative embodiments, the various anatomical features may be differently "weighted" during the comparison process (utilizing various formulaic weightings and/or mathematical algorithms), based on their relative importance or other criteria chosen by the designer/programmer and/or physician.

In a similar manner, the various anatomical features of the tibia (e.g., anterior-posterior and/or medial-lateral dimensions, perimeters, medial/lateral slope, shape, tibial spine height, and other features) can be measured, modeled, and then compared to and/or modified based on a database of one or more "normal" or "healthy" tibial measurement and/or models, with the resulting information used to choose or design a desired implant shape, size and placement. Of course, similar verification of implant appropriateness to the original measured parameters may be accomplished as well.

In a similar manner, the various anatomical features of any joint can be measured and then compared/modified based on a database of "healthy" or otherwise appropriate measurements of appropriate joints, including those of the medial condyle, a lateral condyle, a trochlea, a medial tibia, a lateral tibia, the entire tibia, a medial patella, a lateral patella, an entire patella, a medial trochlea, a central trochlea, a lateral trochlea, a portion of a femoral head, an entire femoral head, a portion of an acetabulum, an entire acetabulum, a portion of a glenoid, an entire glenoid, a portion of a humeral head, an entire humeral head, a portion of an ankle joint, an entire ankle joint, and/or a portion or an entire elbow, wrist, hand, finger, spine, or facet joint.

The patient-specific measurements selected for the evaluation then can be used to select (e.g., from a library), to design, or to select and design an implant component having one or more measurements corresponding to or derived from the one or more of the assessed patient-specific measurements. For example, the implant component can include one or more patient-specific measurements and/or one or more patient-engineered measurements. Optionally, one or more patient-specific models, one or more patient-adapted surgical steps, and/or one or more patient-adapted surgical guide tools also can be selected and/or designed to include one or more measurements corresponding to or derived from the one or more of these patient-specific measurements.

In addition to (or if place of) the above-mentioned measurements, it may be desirable to obtain measurements of the targeted joint (as well as surrounding anatomical areas and or other joints of the patient's anatomy) in a load-bearing or otherwise "real-world" condition. Such measurements can potentially yield extremely useful data on the alignment and/or movement of the joint and surrounding structures (as well as the loading conditions of the various joint components)—information which may be difficult to obtain or model from standard imaging techniques (e.g., sitting or lying X-rays, CT-scans and/or MRI imaging). Such load-bearing measurements can include imaging of the patient standing, walking and/or carrying loads of varying sizes and/or weights.

It may also be desirable to model various of the patient measurements (especially non-load-bearing measurements as described above) to simulate the targeted joint and surrounding anatomy virtually. Such simulations can include virtually modeling the alignment and load bearing condition of the joint and surrounding anatomical structures for the patient standing and/or moving (e.g., walking, running, jumping, squatting, kneeling, walking up and down stairs or inclines/declines, picking up objects, etc.). Such simulations can be used to obtain valuable anatomical, biomechanical and kinematic data including the loaded condition of various joint components, component positions, component movement, joint and/or surrounding tissue anatomical or biomechanical constraints or limitations, as well as estimated mechanical axes in one or more directions (e.g., coronal, sagittal or combinations thereof). This information could then be utilized (alone or in combination with other data described herein) to design various features of a joint resurfacing/replacement implant. This method can be incorporated in the various embodiments described herein as additional patient measurement and anatomical/joint modeling and design data. This analysis is applicable to many different joints, including those of the medial condyle, a lateral condyle, a trochlea, a medial tibia, a lateral tibia, the entire tibia, a medial patella, a lateral patella, an entire patella, a medial trochlea, a central trochlea, a lateral trochlea, a portion of a femoral head, an entire femoral head, a portion of an acetabulum, an entire acetabulum, a portion of a glenoid, an entire glenoid, a portion of a humeral head, an entire humeral head, a portion of an ankle joint, an entire ankle joint, and/or a portion or an entire elbow, wrist, hand, finger, spine, or facet joint.

Historical Patient-Specific Information

In various embodiments described herein, the patient-specific information utilized for selecting and/or designing implant components, guide tools, and/or surgical techniques can include current patient-specific information and/or historical patient-specific information.

As used herein, "current patient-specific information" generally refers to patient-specific information associated with the state of the patient's joint at the time a specific intended treatment (e.g., procedure, implant components, guide tools, surgical technique) for the joint is being considered, selected, and/or designed. In some embodiments, current patient-specific information can be information associated with a patient's joint in a diseased or damaged state. For example, current patient-specific information may be obtained specifically for developing the surgical plan to treat the currently observed diseased or damaged state of the joint. Current patient-specific information can also be information that was initially obtained from the patient's joint prior to a determination that treatment is needed, but rather for evaluation and/or assessment of the current state or condition of the joint, and which is then utilized in subsequent planning of a specific surgical treatment that was deemed necessary based, at least in part, on the evaluation/assessment. In some embodiments, current patient-specific information can be information obtained within about 1 year, within about 6 months, within about 3 months, or within about 30 days of the intended and/or subsequently planned date of the surgical procedure to treat the joint. Additionally or alternatively, current patient-specific information can also simply refer to information obtained after the state of the joint disease or damage for which the patient is being treated reached the state present at the time of the intended treatment.

As used herein, "historical patient-specific information" generally refers to patient-specific information associated with states of the patient's joint at one or more times prior to consideration, selection, and/or design of a specific intended treatment for the joint. In some embodiments, historical patient-specific information can be information associated with a patient's joint in a healthy, pre-diseased, and/or pre-damaged state. Additionally or alternatively, historical patient-specific information can include information associated with the joint in earlier diseased and/or damaged states than the current diseased and/or damaged state of the joint. For example, historical patient-specific information for a patient currently in need of a joint replacement due to disease can include patient-specific information regarding the joint that was obtained when the joint was healthy and/or when the disease was less developed and prior to the need for a joint replacement. In some embodiments, historical patient-specific information can be information obtained greater than about 1 year, about 2 years, about 5 years, about 10 years, or about 20 years before the intended date of the surgical procedure to treat the joint.

Historical patient-specific information may be obtained for a number of reasons. For example, patients eliciting one or more risk factors for a joint problem, such as, for example, low bone mineral density score, may be advised to obtain imaging of one or more joints, even though the joint(s) are currently healthy. In some embodiments, all patients below a certain age, for example, all patients below 40 years of age can be advised to obtain imaging of one or more joints. Further, patients may be advised to obtain imaging of one or more joints at specific and/or regular intervals (e.g., about every 10 years, about every 5 years, about every 2 years, or about every year). Additionally or alternatively, patients may decide on his or her own to have information obtained regarding one or more joints, even though he or she does not have a current, specific need for treatment of the joint(s), in order to have the historical joint information for future use in a treatment, if a need arises. In instances where historical patient-specific information includes information obtained at several different times/ages (e.g., at age 40 and every 5 years thereafter), the historical information may be used to determine the progression of changes to a patient's joint (e.g., due to aging and/or disease), and, optionally, to extrapolate that progression to estimate future states of the joint. Such information regarding the progression of changes to a patient's joint may also be used in selecting and/or designing features for treating the joint. Furthermore, as discussed above, historical patient-specific information for a procedure may have been obtained at the time of an earlier procedure performed on the patient.

Historical patient-specific information can comprise any of the various forms of patient-specific information described herein. For example, in some embodiments, historical patient-specific information can be imaging data associated with a joint. As described elsewhere herein, such imaging data may be obtained from, for example, one or more of x-ray imaging, digital tomosynthesis, cone beam CT, non-spiral or spiral CT, non-isotropic or isotropic MRI, SPECT, PET, ultrasound, laser imaging, and photo-acoustic imaging. As also described elsewhere herein, the imaging data may be obtained under a variety of conditions (e.g., static, moving, load bearing, non-load bearing). Additionally or alternatively, historical patient-specific information can include measurements of biological features of the patient, including, for example, any of the exemplary measurements described above, listed in Table 4, and/or described elsewhere herein. Historical patient-specific information can also include kinematic information, including, for example, any of the exemplary parameters listed in Table 5 below and/or described elsewhere herein, regarding the joint. The kinematic information may be acquired at one or more times prior to the need for treatment, as discussed above. The kinematic information may also be derived at the time the treatment is needed by utilizing other historical patient-specific information (e.g., imaging data, measurements) in kinematic modeling/simulations to determine historical kinematic information.

Historical patient-specific information can also include and/or be updated with changes in the patient's history. This can include changes in body habitus, e.g., changes in weight or height, physical fitness, and/or previous operations.

Historical patient-specific information may be stored in a variety of locations and forms. For example, historical patient-specific information can be compiled by and stored in a database (e.g., as described above) by, for example, a company specializing in storage and/or use of such information (e.g., medical records bank, imaging center, orthopedic implant company). Such a database may be configured to organize and store a single individual's historical patient-specific information or may be configured to organize and store multiple individuals' historical patient-specific information. Such databases may also be configured to store historical patient-specific information in one or multiple forms. For example, images could be stored in, for example, DICOM format (Digital Imaging and Communications in Medicine) in a PACS (Picture Archiving and Communications System). For kinematic data, sampled data points or attribute-value pairs, for example in XML format, could be used. CAD files could be stored in IGES, STEP, STL generic format or a vendor specific format (e.g., SolidWorks, Pro-Engineer, NX, Catia). Other information could be stored in, for example, one or more of a relational or non-relational database, binary files, ASCII files, and/or spreadsheets, depending, optionally, on the kind of data.

Additionally or alternatively, historical patient-specific information may be stored by a patient's particular healthcare provider (e.g., primary care, orthopedic specialist, hospital organization).

Figure 8:
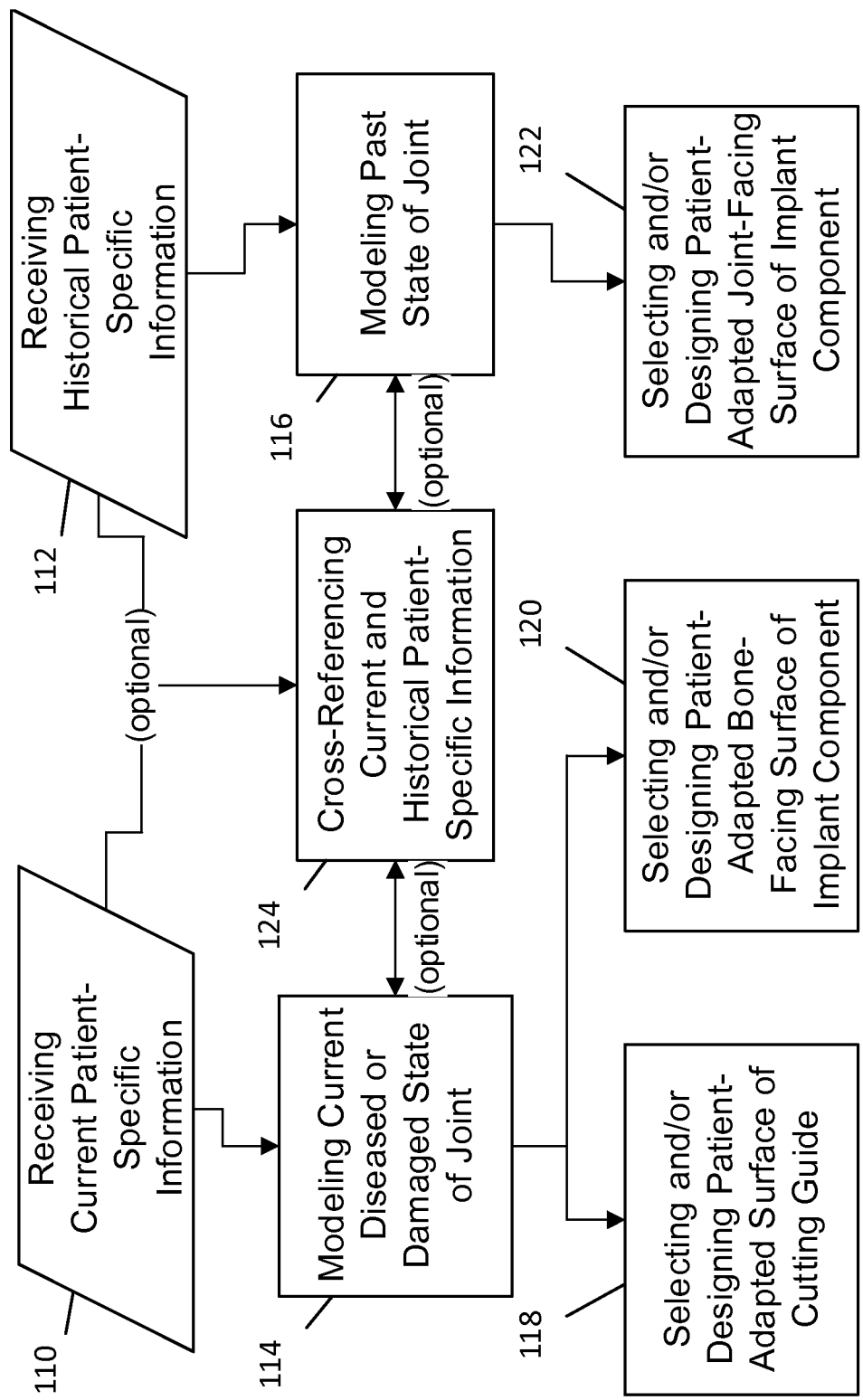
FIG. 8 is a flow chart illustrating a process of making a cutting guide and an implant component using current and historical patient-specific information.

In various embodiments, historical patient-specific information may be used in any of the steps of selecting and/or designing patient-adapted implants, tools, systems, and/or surgical techniques described herein. For example, as shown in the flowchart of FIG. 8, some embodiments can include receiving current patient-specific information 110 and receiving historical patient-specific information 112. Based, at least in part, on the current patient-specific information, the current diseased or damaged state of the joint can be modeled 114. Additionally, based, at least in part, on the historical patient-specific information, a past state of the joint can be modeled 116. A patient-adapted surface of a cutting guide for use in preparing the joint to receive an implant component may be selected and/or designed based, at least in part, on the modeled current state of the joint 118. A patient-adapted bone-facing surface of an implant component may also be selected and/or designed based, at least in part on the current diseased or damaged state of the joint. And a patient-adapted joint-facing surface of the implant component may be selected and/or designed based, at least in part, on the modeled past state of the joint. Further, in some embodiments, historical patient-specific information may be cross-referenced with current patient-specific information 124 in, for example, the manner of cross-referencing described above.

By way of example, in some embodiments, historical patient-specific information can include information regarding the articular shape of the patient's joint in a healthy condition. When the patient's joint becomes diseased and requires replacement, the stored historical information regarding the healthy shape of the patient's joint may then be used to, for example, select and/or design the shape of one or more joint-facing (also referred to herein as "external") surfaces of one or more implant components. Current patient-specific information may be used to select and/or design, for example, portions of the surgical technique, bone cuts, cut guides, and bone-facing (also referred to herein as "internal") surfaces of the implant component(s). This combination can result in implant components with both improved fit and coverage, as well as improved and/or more natural kinematics (e.g., better replicating the function of the patient's healthy joint).

Generating a Model of a Joint

In certain embodiments, one or more models of at least a portion of a patient's joint can be generated. Specifically, the patient-specific data and/or measurements described above can be used to generate a model that includes at least a portion of the patient's joint. Optionally, one or more patient-engineered resection cuts, one or more drill holes, one or more patient-adapted guide tools, and/or one or more patient-adapted implant components can be included in a model. In certain embodiments, a model of at least part of a patient's joint can be used to directly generate a patient-engineered resection cut strategy, a patient-adapted guide tool design, and/or a patient-adapted implant component design for a surgical procedure (e.g., without the model itself including one or more resection cuts, one or more drill holes, one or more guide tools, and/or one or more implant components). In certain embodiments, the model that includes at least a portion of the patient's joint also can include or display, as part of the model, one or more resection cuts, one or more drill holes, (e.g., on a model of the patient's femur), one or more guide tools, and/or one or more implant components that have been designed for the particular patient using the model. Moreover, one or more resection cuts, one or more drill holes, one or more guide tools, and/or one or more implant components can be modeled and selected and/or designed separate from a model of a particular patient's biological feature.

Figure 5:
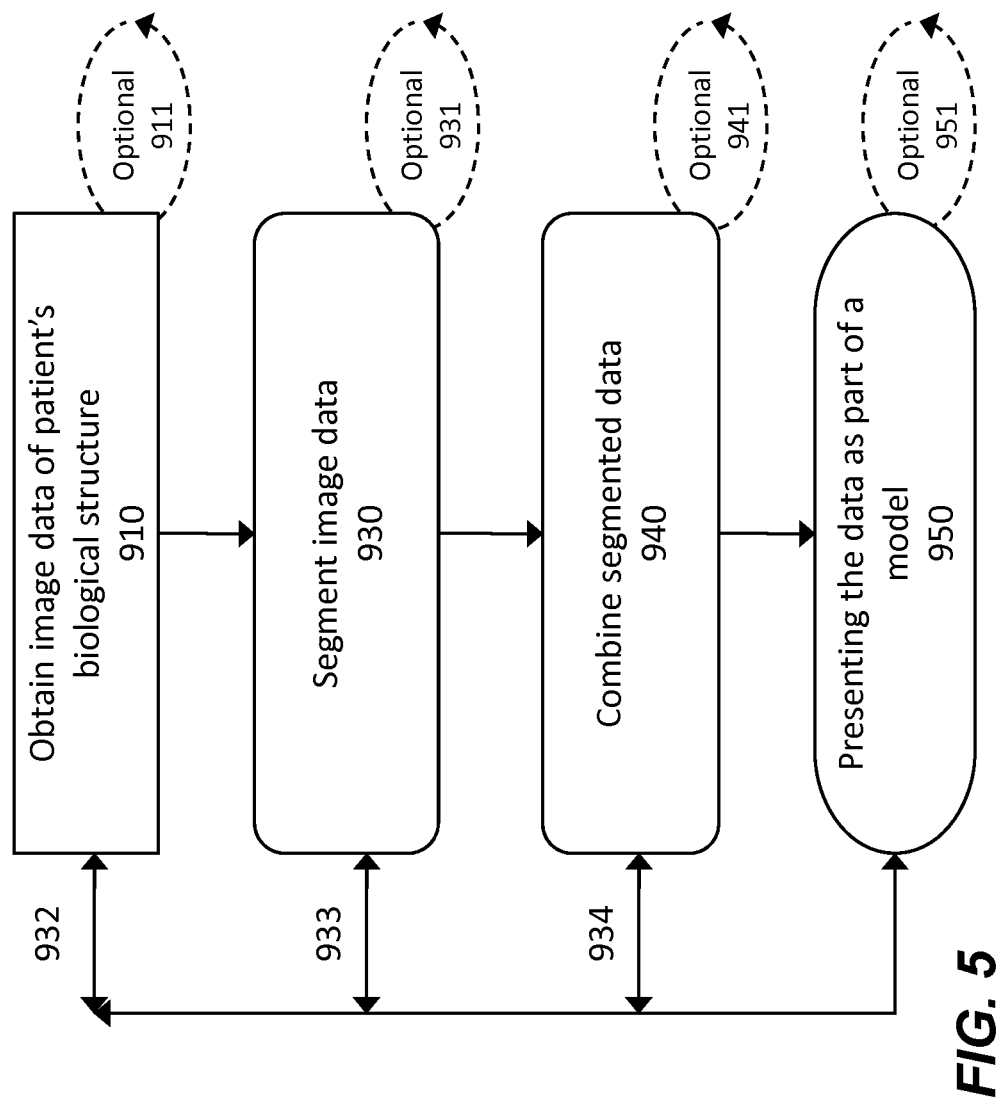
FIG. 5 is a flow chart illustrating a process for generating a model of a patient's joint (and/or a resection cut, guide tool, and/or implant component)

Various methods can be used to generate a model. As illustrated in FIG. 5, in certain embodiments the method of generating a model of a patient's joint (and/or a resection cut, drill hole, guide tool, and/or implant component) or other biological feature (and/or a patient-specific feature of a guide tool or implant component) can include one or more of the steps of obtaining image data of a patient's biological structure 910; segmenting the image data 930; combining the segmented data 940; and presenting the data as part of a model 950.

Image data can be obtained 910 from near or within the patient's biological structure of interest. For example, pixel or voxel data from one or more radiographic or tomographic images of a patient's joint can be obtained, for example, using computed or magnetic resonance tomography. Other imaging modalities known in the art such as ultrasound, laser imaging, PET, SPECT, radiography including digital radiography, digital tomosynthesis, cone beam CT, and contrast enhanced imaging can be used.

Modeling and Addressing Joint Defects

In certain embodiments, the reference points and/or measurements described above can be processed using mathematical functions to derive virtual, corrected features, which may represent a restored, ideal or desired feature from which a patient-adapted implant component can be designed. For example, one or more features, such as surfaces or dimensions of a biological structure can be modeled, altered, added to, changed, deformed, eliminated, corrected and/or otherwise manipulated (collectively referred to herein as "variation" of an existing surface or structure within the joint). While it is described in the knee, these embodiments can be applied to any joint or joint surface in the body, e.g. a knee, hip, ankle, foot, toe, shoulder, elbow, wrist, hand, and a spine or spinal joints.

Variation of the joint or portions of the joint can include, without limitation, variation of one or more external surfaces, internal surfaces, joint-facing surfaces, uncut surfaces, cut surfaces, altered surfaces, and/or partial surfaces as well as osteophytes, subchondral cysts, geodes or areas of eburnation, joint flattening, contour irregularity, and loss of normal shape. The surface or structure can be or reflect any surface or structure in the joint, including, without limitation, bone surfaces, ridges, plateaus, cartilage surfaces, ligament surfaces, or other surfaces or structures. The surface or structure derived can be an approximation of a healthy joint surface or structure or can be another variation. The surface or structure can be made to include pathological alterations of the joint. The surface or structure also can be made whereby the pathological joint changes are virtually removed in whole or in part.

Once one or more reference points, measurements, structures, surfaces, models, or combinations thereof have been selected or derived, the resultant shape can be varied, deformed or corrected. In certain embodiments, the variation can be used to select and/or design an implant component having an ideal or optimized feature or shape, e.g., corresponding to the deformed or corrected joint feature or shape. For example, in one application of this embodiment, historical patient-specific information, as described above, may be used to derive an ideal or optimized implant shape that may reflect the shape of the patient's joint before he or she developed arthritis.

Alternatively or in addition, the variation can be used to select and/or design a patient-adapted surgical procedure to address the deformity or abnormality. For example, the variation can include surgical alterations to the joint, such as virtual resection cuts, virtual drill holes, virtual removal of osteophytes, and/or virtual building of structural support in the joint deemed necessary or beneficial to a desired final outcome for a patient.

Corrections can be used to address osteophytes, subchondral voids, and other patient-specific defects or abnormalities. In certain embodiments, correction can include the virtual removal of tissue, for example, to address an articular defect, to remove subchondral cysts, and/or to remove diseased or damaged tissue (e.g., cartilage, bone, or other types of tissue), such as osteochondritic tissue, necrotic tissue, and/or torn tissue. In such embodiments, the correction can include the virtual removal of the tissue (e.g., the tissue corresponding to the defect, cyst, disease, or damage) and the bone-facing surface of the implant component can be derived after the tissue has been virtually removed. In certain embodiments, the implant component can be selected and/or designed to include a thickness or other features that substantially matches the removed tissue and/or optimizes one or more parameters of the joint. Optionally, a surgical strategy and/or one or more guide tools can be selected and/or designed to reflect the correction and correspond to the implant component.

Modeling Proper Limb Alignment

Proper joint and limb function depend on correct limb alignment. For example, in repairing a knee joint with one or more knee implant components, optimal functioning of the new knee depends on the correct alignment of the anatomical and/or mechanical axes of the lower extremity. Accordingly, an important consideration in designing and/or replacing a natural joint with one or more implant components is proper limb alignment or, when the malfunctioning joint contributes to a misalignment, proper realignment of the limb.

Certain embodiments described herein include collecting and using data from imaging tests to virtually determine in one or more planes one or more of an anatomic axis and a mechanical axis and the related misalignment of a patient's limb. The misalignment of a limb joint relative to the axis can identify the degree of deformity, for example, varus or valgus deformity in the coronal plane or genu antecurvatum or recurvatum deformity in the sagittal plane. Then, one or more of the patient-specific implant components and/or the implant procedure steps, such as bone resection, can be designed to help correct the misalignment.

The imaging tests that can be used to virtually determine a patient's axis and misalignment can include one or more of the various imaging modalities described above, such as, for example, x-ray imaging, digital tomosynthesis, cone beam CT, non-spiral or spiral CT, non-isotropic or isotropic MRI, SPECT, PET, ultrasound, laser imaging, and photoacoustic imaging, including studies utilizing contrast agents. Data from these tests can be used to determine anatomic reference points or limb alignment, including alignment angles within the same and between different joints or to simulate normal limb alignment. Any anatomic features related to the misalignment can be selected and imaged. For example, in certain embodiments, such as for a knee or hip implant, the imaging test can include data from at least one of, or several of, a hip joint, knee joint and ankle joint. The imaging test can be obtained in lying, prone, supine or standing position. The imaging test can include only the target joint, or both the target joint and also selected data through one or more adjoining joints.

Using the image data, one or more mechanical or anatomical axes, angles, planes or combinations thereof can be determined. In certain embodiments, such axes, angles, and/or planes can include, or be derived from, one or more of a Whiteside's line, Blumensaat's line, transepicondylar line, femoral shaft axis, femoral neck axis, acetabular angle, lines tangent to the superior and inferior acetabular margin, lines tangent to the anterior or posterior acetabular margin, femoral shaft axis, tibial shaft axis, transmalleolar axis, posterior condylar line, tangent(s) to the trochlea of the knee joint, tangents to the medial or lateral patellar facet, lines tangent or perpendicular to the medial and lateral posterior condyles, lines tangent or perpendicular to a central weight-bearing zone of the medial and lateral femoral condyles, lines transecting the medial and lateral posterior condyles, for example through their respective centerpoints, lines tangent or perpendicular to the tibial tuberosity, lines vertical or at an angle to any of the aforementioned lines, and/or lines tangent to or intersecting the cortical bone of any bone adjacent to or enclosed in a joint. Moreover, estimating a mechanical axis, an angle, or plane also can be performed using image data obtained through two or more joints, such as the knee and ankle joint, for example, by using the femoral shaft axis and a centerpoint or other point in the ankle, such as a point between the malleoli.

As one example, if surgery of the knee or hip is contemplated, the imaging test can include acquiring data through at least one of, or several of, a hip joint, knee joint or ankle joint. As another example, if surgery of the knee joint is contemplated, a mechanical axis can be determined. For example, the centerpoint of the hip knee and ankle can be determined. By connecting the centerpoint of the hip with that of the ankle, a mechanical axis can be determined in the coronal plane. The position of the knee relative to said mechanical axis can be a reflection of the degree of varus or valgus deformity. The same determinations can be made in the sagittal plane, for example to determine the degree of genu antecurvatum or recurvatum. Similarly, any of these determinations can be made in any other desired planes, in two or three dimensions.

Additionally or alternatively, in some embodiments, a proper limb alignment may be determined based, at least in part, on historical patient-specific information, as described above. For example, the historical patient-specific information may include information regarding the limb alignment prior to, or at an early state of, disease or damage of relevant joints.

Once the proper alignment of the patient's extremity has been determined virtually, one or more surgical steps (e.g., resection cuts) may be planned and/or accomplished, which may include the use of surgical tools (e.g., tools to guide the resection cuts), and/or implant components (e.g., components having variable thicknesses to address misalignment).

Modeling Articular Cartilage

Cartilage loss in one compartment can lead to progressive joint deformity. For example, cartilage loss in a medial compartment of the knee can lead to varus deformity. In certain embodiments, cartilage loss can be estimated in the affected compartments. The estimation of cartilage loss can be done using an ultrasound, MRI, or CT scan or other imaging modality, optionally with intravenous or intra-articular contrast. The estimation of cartilage loss can be as simple as measuring or estimating the amount of joint space loss seen on x-rays. For the latter, typically standing x-rays are preferred. If cartilage loss is measured from x-rays using joint space loss, cartilage loss on one or two opposing articular surfaces can be estimated by, for example, dividing the measured or estimated joint space loss by two to reflect the cartilage loss on one articular surface. Other ratios or calculations are applicable depending on the joint or the location within the joint. Subsequently, a normal cartilage thickness can be virtually established on one or more articular surfaces by simulating normal cartilage thickness. In this manner, a normal or near normal cartilage surface can be derived. Normal cartilage thickness can be virtually simulated using a computer, for example, based on computer models, for example using the thickness of adjacent normal cartilage, cartilage in a contralateral joint, or other anatomic information including subchondral bone shape or other articular geometries. Cartilage models and estimates of cartilage thickness can also be derived from anatomic reference databases that can be matched, for example, to a patient's weight, sex, height, race, gender, or articular geometry(ies).

Additionally or alternatively, in some embodiments, cartilage models and estimates of cartilage thickness can also be derived from, at least in part, historical patient-specific information, as described above. For example, the historical patient-specific information may include information regarding cartilage thickness when the relevant joint was healthy, or in one or more early states of disease or damage.

In certain embodiments, a patient's limb alignment can be virtually corrected by realigning the knee after establishing a normal cartilage thickness or shape in the affected compartment by moving the joint bodies, for example, femur and tibia, so that the opposing cartilage surfaces including any augmented or derived or virtual cartilage surface touch each other, typically in the preferred contact areas. These contact areas can be simulated for various degrees of flexion or extension.

Parameters for Selecting and/or Designing a Patient-Adapted Implant

The patient-adapted implants (e.g., implants having one or more patient-specific and/or patient-engineered features) of certain embodiments can be designed based on patient-specific data to optimize one or more parameters including, but not limited to: (1) deformity correction and limb alignment (2) maximum preservation of bone, cartilage, or ligaments, (3) preservation and/or optimization of features of the patient's biology, such as trochlea and trochlear shape, (4) restoration and/or optimization of joint kinematics, and (5) restoration or optimization of joint-line location and/or joint gap width. Various features of an implant component that can be designed or engineered based on the patient-specific data to help meet any number of user-defined thresholds for these parameters. The features of an implant that can be designed and/or engineered patient-specifically can include, but are not limited to, (a) implant shape, external and internal, (b) implant size, (c) and implant thickness.

There are several advantages that a patient-specific implant designed and/or engineered to meet or improve one of more of these parameters can have over a traditional implant. These advantages can include, for example: improved mechanical stability of the extremity; opportunity for a pre-primary or additional revision implant; improved fit with existing or modified biological features; improved motion and kinematics, and other advantages.

Establishing Normal or Near-Normal Joint Kinematics

In certain embodiments, bone cuts and implant shape including at least one of a bone-facing or a joint-facing surface of the implant can be designed or selected to achieve normal joint kinematics.

In certain embodiments, a computer program simulating biomotion of one or more joints, such as, for example, a knee joint, or a knee and ankle joint, or a hip, knee and/or ankle joint can be utilized. In certain embodiments, patient-specific imaging data can be fed into this computer program. For example, a series of two-dimensional images of a patient's knee joint or a three-dimensional representation of a patient's knee joint can be entered into the program. Additionally, two-dimensional images or a three-dimensional representation of the patient's ankle joint and/or hip joint may be added.

Alternatively, patient-specific kinematic data, for example obtained in a gait lab, can be fed into the computer program. Alternatively, patient-specific navigation data, for example generated using a surgical navigation system, image guided or non-image guided can be fed into the computer program. This kinematic or navigation data can, for example, be generated by applying optical or RF markers to the limb and by registering the markers and then measuring limb movements, for example, flexion, extension, abduction, adduction, rotation, and other limb movements.

In some embodiments, the patient-specific information referred to above that is used to create the biomotion model can be current patient-specific information. Additionally or alternatively, in some embodiments, historical patient-specific information, as described above, can be used to create the biomotion model and/or determine patient-specific kinematic information. Thus, in some embodiments, historical patient-specific information may be used to determine kinematic information regarding a joint in a healthy or pre-diseased or pre-damaged state.

Optionally, other data including anthropometric data may be added for each patient. These data can include but are not limited to the patient's age, gender, weight, height, size, body mass index, and race. Desired limb alignment and/or deformity correction can be added into the model. The position of bone cuts on one or more articular surfaces as well as the intended location of implant bearing surfaces on one or more articular surfaces can be entered into the model.

A patient-specific biomotion model can be derived that includes combinations of parameters listed above. The biomotion model can simulate various activities of daily life including normal gait, stair climbing, descending stairs, running, kneeling, squatting, sitting and any other physical activity. The biomotion model can start out with standardized activities, typically derived from reference databases. These reference databases can be, for example, generated using biomotion measurements using force plates and motion trackers using radiofrequency or optical markers and video equipment.

The biomotion model can then be individualized with use of patient-specific information including at least one of, but not limited to the patient's age, gender, weight, height, body mass index, and race, the desired limb alignment or deformity correction, and the patient's imaging data, for example, a series of two-dimensional images or a three-dimensional representation of the joint for which surgery is contemplated.

An implant shape including associated bone cuts generated in the preceding optimizations, for example, limb alignment, deformity correction, bone preservation on one or more articular surfaces, can be introduced into the model. Table 5 includes an exemplary list of parameters that can be measured in a patient-specific biomotion model.

TABLE 5

Parameters measured in a patient-specific biomotion model for various implants

| Joint implant | Measured Parameter |
|---|---|
| knee | Medial femoral rollback during flexion |
| knee | Lateral femoral rollback during flexion |
| knee | Patellar position, medial, lateral, superior, inferior for different flexion and extension angles |
| knee | Internal and external rotation of one or more femoral condyles |
| knee | Internal and external rotation of the tibia |
| knee | Flexion and extension angles of one or more articular surfaces |
| knee | Anterior slide and posterior slide of at least one of the medial and lateral femoral condyles during flexion or extension |
| knee | Medial and lateral laxity throughout the range of motion |
| knee | Contact pressure or forces on at least one or more articular surfaces, e.g. a femoral condyle and a tibial plateau, a trochlea and a patella |
| knee | Contact area on at least one or more articular surfaces, e.g. a femoral condyle and a tibial plateau, a trochlea and a patella |
| knee | Forces between the bone-facing surface of the implant, an optional cement interface and the adjacent bone or bone marrow, measured at least one or multiple bone cut or bone-facing surface of the implant on at least one or multiple articular surfaces or implant components. |
| knee | Ligament location, e.g. ACL, PCL, MCL, LCL, retinacula, joint capsule, estimated or derived, for example using an imaging test. |
| knee | Ligament tension, strain, shear force, estimated failure forces, loads for example for different angles of flexion, extension, rotation, abduction, adduction, with the different positions or movements optionally simulated in a virtual environment. |
| knee | Adduction/abduction moments, flexion/extension moments, internal/external rotation moments |
| knee | Potential implant impingement on other articular structures, e.g. in high flexion, high extension, internal or external rotation, abduction or adduction or any combinations thereof or other angles/positions/movements. |
| Hip, shoulder or other joint | Internal and external rotation of one or more articular surfaces |
| Hip, shoulder or other joint | Flexion and extension angles of one or more articular surfaces |
| Hip, shoulder or other joint | Anterior slide and posterior slide of at least one or more articular surfaces during flexion or extension, abduction or adduction, elevation, internal or external rotation |
| Hip, shoulder or other joint | Joint laxity throughout the range of motion |
| Hip, shoulder or other joint | Contact pressure or forces on at least one or more articular surfaces, e.g. an acetabulum and a femoral head, a glenoid and a humeral head |
| Hip, shoulder or other joint | Forces between the bone-facing surface of the implant, an optional cement interface and the adjacent bone or bone marrow, measured at least one or multiple bone cut or bone-facing surface of the implant on at least one or multiple articular surfaces or implant components. |
| Hip, shoulder or other joint | Ligament location, e.g. transverse ligament, glenohumeral ligaments, retinacula, joint capsule, estimated or derived, for example using an imaging test. |
| Hip, shoulder or other joint | Ligament tension, strain, shear force, estimated failure forces, loads for example for different angles of flexion, extension, rotation, abduction, adduction, with the different positions or movements optionally simulated in a virtual environment. |
| Hip, shoulder or other joint | Potential implant impingement on other articular structures, e.g. in high flexion, high extension, internal or external rotation, abduction or adduction or elevation or any combinations thereof or other angles/positions/movements. |

The above list is not meant to be exhaustive, but only exemplary. Any other biomechanical parameter known in the art can be included in the analysis.

The resultant biomotion data can be used to further optimize the implant design with the objective to establish normal or near normal kinematics. The implant optimizations can include one or multiple implant components. Implant optimizations based on patient-specific data including image based biomotion data include, but are not limited to:

Changes to external, joint-facing implant shape in coronal plane

Changes to external, joint-facing implant shape in sagittal plane

Changes to external, joint-facing implant shape in axial plane

Changes to external, joint-facing implant shape in multiple planes or three dimensions Changes to internal, bone-facing implant shape in coronal plane Changes to internal, bone-facing implant shape in sagittal plane Changes to internal, bone-facing implant shape in axial plane Changes to internal, bone-facing implant shape in multiple planes or three dimensions Changes to one or more bone cuts, for example with regard to depth of cut, orientation of cut Any single one or combinations of the above or all of the above on at least one articular surface or implant component or multiple articular surfaces or implant components.

Restoration or Optimization of Joint-Line Location and Joint Gap Width

Certain embodiments are directed to implant components, and related designs and methods, having one or more features that are engineered from patient-specific data to restore or optimize the particular patient's joint-line location. In addition or alternatively, certain patient-specific implant components, and related designs and methods, can have one or more features that are engineered from patient-specific data to restore or optimize the particular patient's joint gap width.

Figure 6:
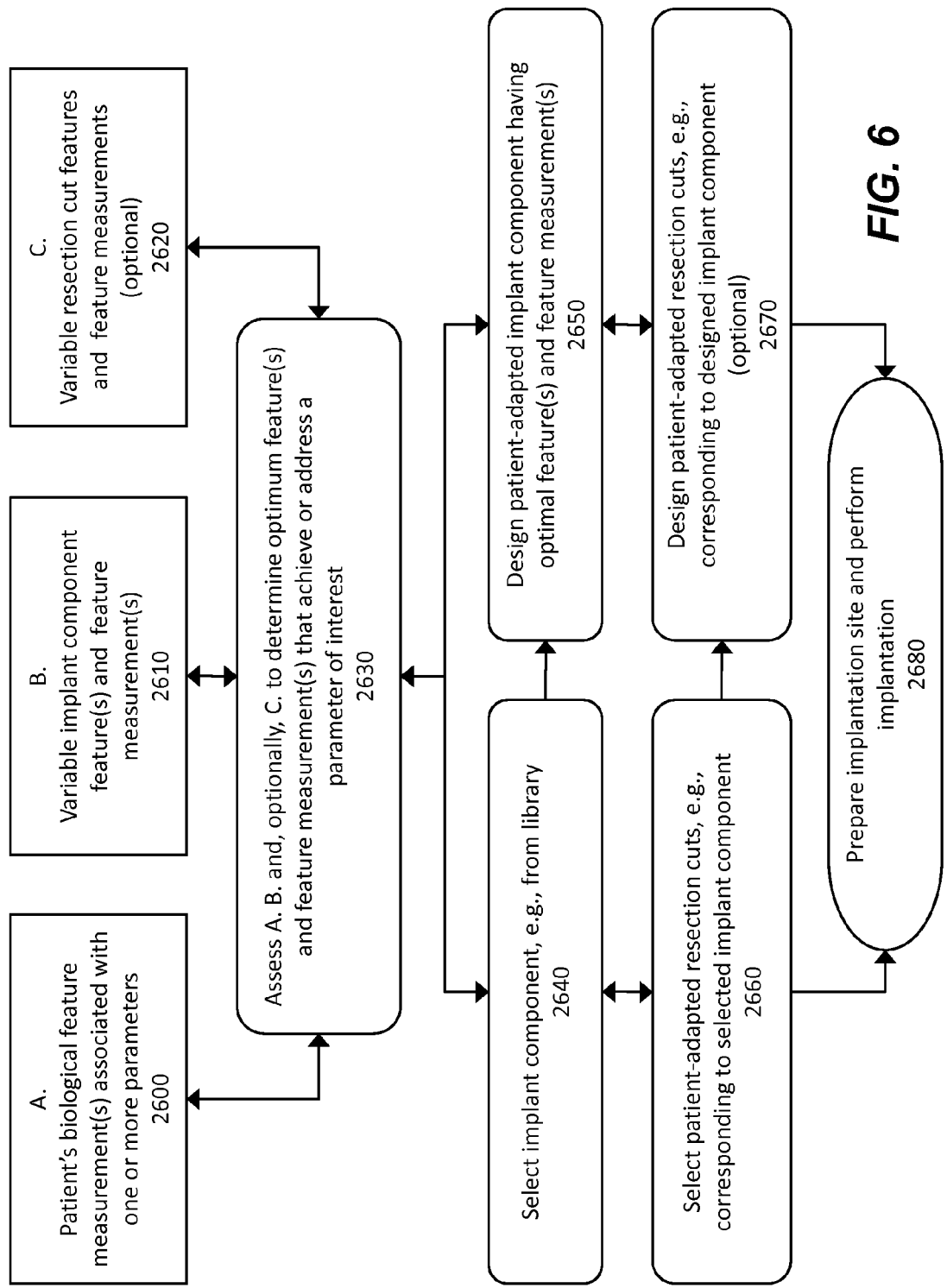
FIG. 6 is a flow chart illustrating a process of assessing and selecting and/or designing one or more implant component features and/or feature measurements, and, optionally assessing and selecting and/or designing one or more resection cut features and feature measurements, for a particular patient.

FIG. 6 is a flow chart illustrating the process of assessing and selecting and/or designing one or more implant component features and/or feature measurements, and, optionally assessing and selecting and/or designing one or more resection cut features and feature measurements, for a particular patient. Using the techniques described herein or those suitable and known in the art, one or more of the patient's biological features and/or feature measurements are obtained 2600. In addition, one or more variable implant component features and/or feature measurements are obtained 2610. Optionally, one or more variable resection cut features and/or feature measurements are obtained 2620. Moreover, one or more variable guide tool features and/or feature measurements also can optionally be obtained. Each one of these step can be repeated multiple times, as desired.

The obtained patient's biological features and feature measurements, implant component features and feature measurements, and, optionally, resection cut and/or guide tool features and/or feature measurements then can be assessed to determine the optimum implant component features and/or feature measurements, and optionally, resection cut and/or guide tool features and/or feature measurements, that achieve one or more target or threshold values for parameters of interest 2630 (e.g., by maintaining or restoring a patient's healthy joint feature). As noted, parameters of interest can include, for example, one or more of (1) joint deformity correction; (2) limb alignment correction; (3) bone, cartilage, and/or ligaments preservation at the joint; (4) preservation, restoration, or enhancement of one or more features of the patient's biology, for example, trochlea and trochlear shape; (5) preservation, restoration, or enhancement of joint kinematics, including, for example, ligament function and implant impingement; (6) preservation, restoration, or enhancement of the patient's joint-line location and/or joint gap width; and (7) preservation, restoration, or enhancement of other target features. This step can be repeated as desired. For example, the assessment step 2630 can be reiteratively repeated after obtaining various feature and feature measurement information 2600, 2610, 2620.

Once the one or more optimum implant component features and/or feature measurements are determined, the implant component(s) can be selected 2640, designed 2650, or selected and designed 2640, 2650. For example, an implant component having some optimum features and/or feature measurements can be designed using one or more CAD software programs or other specialized software to optimize additional features or feature measurements of the implant component. One or more manufacturing techniques described herein or known in the art can be used in the design step to produce the additional optimized features and/or feature measurements. This process can be repeated as desired.

Optionally, one or more resection cut features and/or feature measurements can be selected 2660, designed 2670, or selected and further designed 2660, 2670. For example, a resection cut strategy selected to have some optimum features and/or feature measurements can be designed further using one or more CAD software programs or other specialized software to optimize additional features or measurements of the resection cuts, for example, so that the resected surfaces substantially match optimized bone-facing surfaces of the selected and designed implant component. This process can be repeated as desired.

Once optimum features and/or feature measurements for the implant component, and optionally for the resection cuts and/or guide tools, have been selected and/or designed, the implant site can be prepared, for example by removing cartilage and/or resectioning bone from the joint surface, and the implant component can be implanted into the joint 2680.

Figure 7:
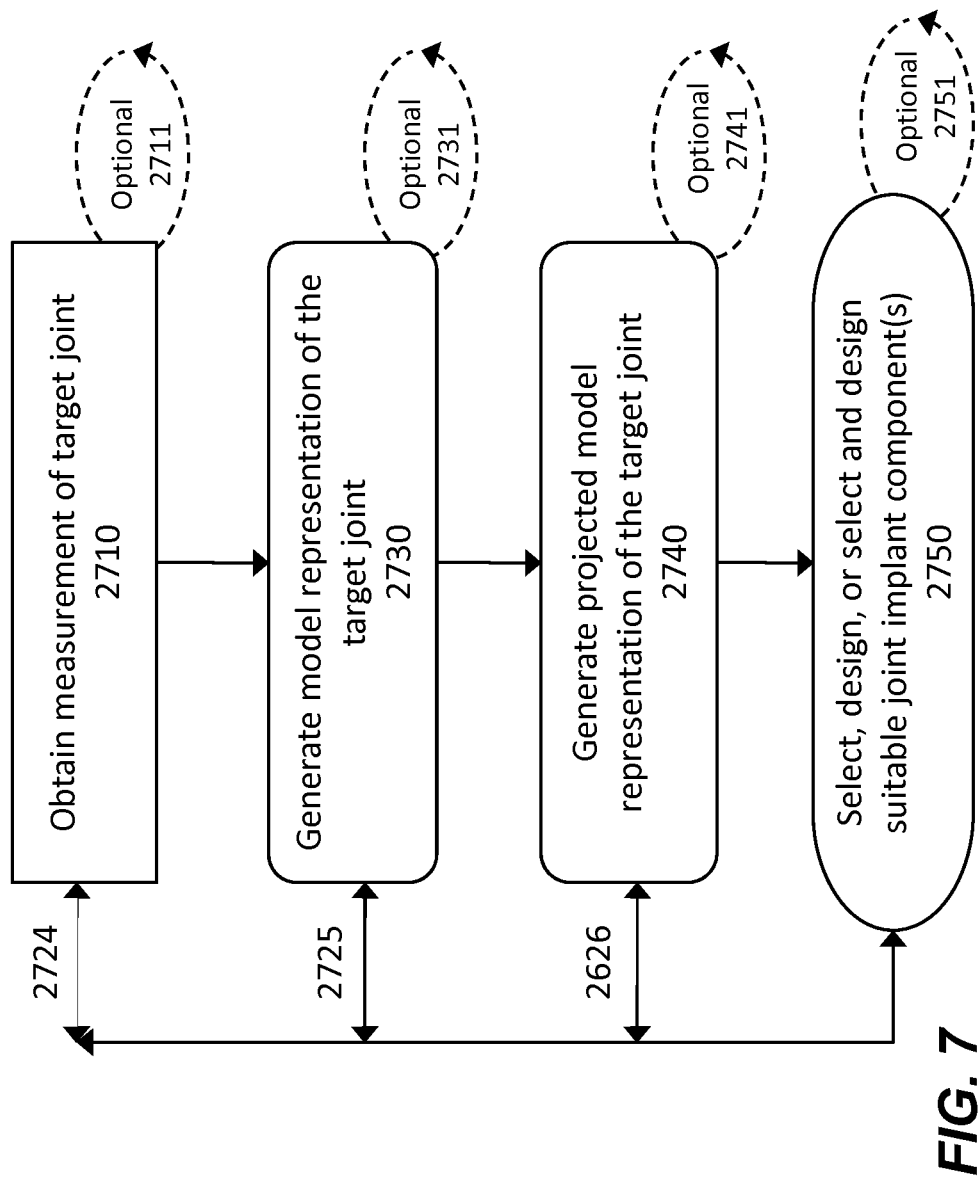
FIG. 7 is a flow chart illustrating a process for assessing a joint and selecting and/or designing a suitable replacement implant component.

FIG. 7 is an illustrative flow chart showing exemplary steps taken by a practitioner in assessing a joint and selecting and/or designing a suitable replacement implant component. First, a practitioner obtains a measurement of a target joint 2710. The step of obtaining a measurement can be accomplished, for example, based on an image of the joint. This step can be repeated 2711 as necessary to obtain a plurality of measurements, for example, from one or more images of the patient's joint, in order to further refine the joint assessment process. Once the practitioner has obtained the necessary measurements, the information can be used to generate a model representation of the target joint being assessed 2730. This model representation can be in the form of a topographical map or image. The model representation of the joint can be in one, two, or three dimensions. It can include a virtual model and/or a physical model. More than one model can be created 2731, if desired. Either the original model, or a subsequently created model, or both can be used.

After the model representation of the joint is generated 2730, the practitioner optionally can generate a projected model representation of the target joint in a corrected condition 2740, e.g., based on historical patient-specific information regarding the joint (as described above), based on an image of the patient's contralateral healthy joint, based on a projected image of a surface that negatively-matches the opposing surface, or a combination thereof. This step can be repeated 2741, as necessary or as desired. Using the difference between the topographical condition of the joint and the projected image of the joint, the practitioner can then select a joint implant 2750 that is suitable to achieve the corrected joint anatomy. As will be appreciated by those of skill in the art, the selection and/or design process 2750 can be repeated 2751 as often as desired to achieve the desired result. Additionally, it is contemplated that a practitioner can obtain a measurement of a target joint 2710 by obtaining, for example, an x-ray, and then selects a suitable joint replacement implant 2750.

One or more of these steps can be repeated reiteratively 2724, 2725, 2726. Moreover, the practitioner can proceed directly from the step of generating a model representation of the target joint 2730 to the step of selecting a suitable joint implant component 2750. Additionally, following selection and/or design of the suitable joint implant component 2750, the steps of obtaining measurement of a target joint 2710, generating model representation of target joint 2730 and generating projected model 40, can be repeated in series or parallel as shown by the flow 2724, 2725, 2726.

The term "implant component" as used herein can include: (i) one of two or more devices that work together in an implant or implant system, or (ii) a complete implant or implant system, for example, in embodiments in which an implant is a single, unitary device. The term "match" as used herein is envisioned to include one or both of a negative-match, as a convex surface fits a concave surface, and a positive-match, as one surface is identical to another surface.

Various embodiments described herein can be applicable to any joint, including, without limitation, a spine, spinal articulations, an intervertebral disk, a facet joint, a shoulder, an elbow, a wrist, a hand, a finger, a hip, a knee, an ankle, a foot, or a toe joint. For example, certain embodiments of the obtaining and using historical patient-specific information, implants, guide tools, and related methods of designing (e.g., designing and making), and using the implants and guide tools described herein can be applied to any joint. Furthermore, various embodiments described herein can apply to methods and procedures, and the design of methods and procedures, for resectioning the patient's anatomy in order to implant the implant components described herein and/or to using the guide tools described herein.

What is claimed is:

1. A method of making an implant component for intended treatment of a diseased or damaged joint of a patient, the method comprising:
    receiving current patient-specific information associated with the joint;
    receiving historical patient-specific information associated with the joint; and
    selecting and/or designing an implant component based, at least in part, on the current patient-specific information and the historical patient-specific information.

2. The method of claim 1, wherein the selecting and/or designing comprises selecting and/or designing at least a portion of a joint-facing surface of the implant component based, at least in part, on the historical patient-specific information.

3. The method of claim 1, wherein the selecting and/or designing comprises selecting and/or designing at least a portion of a bone-facing surface of the implant component based, at least in part, on the current patient-specific information.

4. The method of claim 1, wherein the current patient-specific information comprises information associated with the joint in its diseased or damaged state.

5. The method of claim 1, wherein the historical patient-specific information comprises information associated with the joint in a pre-diseased or pre-damaged state.

6. The method of claim 1, wherein the historical patient-specific information comprises information associated with the joint in a diseased or damaged state that preceded the diseased or damaged state with which the current patient-specific information is associated.

7. The method of claim 1, wherein the historical patient-specific information comprises information associated with states of the joint at two or more times prior to the state of the joint with which the current patient-specific information is associated.

8. The method of claim 1, wherein the current and/or historical patient-specific information comprises image data associated with the joint.

9. The method of claim 1, wherein the current and/or historical patient-specific information comprises kinematic information associated with the joint.

10. The method of claim 1, wherein the current and/or historical patient-specific information consists of one or more parameters selected from the group of parameters consisting of a dimension associated with the joint, a curvature associated with a joint-facing surface of the joint, and combinations thereof.

11. The method of claim 1, further comprising deriving the current and/or historical patient-specific information from image data associated with the joint.

12. The method of claim 1, wherein the current patient-specific information comprises information associated with a state of the joint at a time within about 3 months of the intended treatment of the diseased or damaged joint.

13. The method of claim 1, wherein the historical patient specific-specific information comprises information associated with one or more states of the joint at one or more times greater than about 1 year prior to the intended treatment of the diseased or damaged joint.

14. An implant component for treating a patient's joint, the implant component comprising:
    a joint-facing surface having a patient-adapted dimension based, at least in part, on historical patient-specific information associated with the joint; and
    a bone-facing surface having a patient-adapted dimension based, at least in part, on current patient-specific information associated with the joint.

15. A system for treating a patient's joint, comprising:
    the implant of claim 14; and
    a cutting guide including a patient-adapted surface configured to engage at least a portion of a surface of the joint, wherein the patient-adapted surface includes a shape based, at least in part, on current patient-specific information associated with the joint.

16. A method of providing historical patient-specific information for selecting and/or designing a treatment for a diseased or damaged joint of a patient, comprising:
    receiving a first set of patient-specific information associated with a first state of at least a portion of the patient's anatomy;
    storing the first set of patient-specific information in a library of historical patient-specific information; and
    providing at least a portion of the historical patient-specific information for selecting and/or designing a treatment for the joint,
    wherein the first set of patient-specific information comprises information obtained from the patient prior to the diseased or damaged state of the joint.

17. The method of claim 16, further comprising:
    receiving one or more additional sets of patient-specific information associated with at least a portion of the patient's anatomy; and
    storing the one or more additional sets of patient-specific information in the library of historical patient-specific information,
    wherein the one or more additional sets of patient-specific information are each associated with a state of at least a portion of the patient's anatomy at a distinct time.

18. The method of claim 16, wherein the storing step comprises storing the first set of patient-specific information in the library of historical patient-specific information for at least one year prior to the providing step.

19. The method of claim 16, wherein the patient-specific information comprises image data associated with the joint.

20. The method of claim 16, wherein the patient-specific information comprises kinematic information associated with the joint.

* * * * *